United States Patent
Huang et al.

(10) Patent No.: US 10,115,910 B2
(45) Date of Patent: Oct. 30, 2018

(54) ORGANIC ELECTROLUMINESCENT MATERIAL, ORGANIC ELECTROLUMINESCENT DEVICE AND QUANTUM DOT ELECTROLUMINESCENT UNIT

(71) Applicants: HannStar Display (Nanjing) Corporation, Nanjing (CN); HANNSTAR DISPLAY CORPORATION, Taipei (TW)

(72) Inventors: Jau-Jiun Huang, Taipei (TW); Man-Kit Leung, Taipei (TW); Yu-Lin Chiang, Taipei (TW); Jiun-Haw Lee, Taipei (TW)

(73) Assignees: HANNSTAR DISPLAY (NANJING) CORPORATION, Nanjing (CN); HANNSTAR DISPLAY CORPORATION, Taipei (TW)

(*) Notice: Subject to any disclaimer, the term of this patent is extended or adjusted under 35 U.S.C. 154(b) by 244 days.

(21) Appl. No.: 15/089,092

(22) Filed: Apr. 1, 2016

(65) Prior Publication Data

US 2016/0293857 A1   Oct. 6, 2016

(30) Foreign Application Priority Data

Apr. 3, 2015  (CN) .......................... 2015 1 0158326
Apr. 3, 2015  (CN) .......................... 2015 1 0158919

(51) Int. Cl.
*H01L 51/00* (2006.01)
*C09K 11/06* (2006.01)
(Continued)

(52) U.S. Cl.
CPC ........ *H01L 51/0072* (2013.01); *C07D 403/10* (2013.01); *C07D 403/14* (2013.01);
(Continued)

(58) Field of Classification Search
CPC .................................................. H01L 51/0072
See application file for complete search history.

(56) References Cited

U.S. PATENT DOCUMENTS 9,276,046 B2 * 3/2016 Liu .................. H01L 51/502
9,666,822 B2 * 5/2017 Forrest .............. H01L 51/5024
(Continued)

FOREIGN PATENT DOCUMENTS

CN          101889480 A      11/2010

*Primary Examiner* — Michael M Dollinger
(74) *Attorney, Agent, or Firm* — Muncy, Geissler, Olds & Lowe, P.C.

(57) ABSTRACT

An organic electroluminescent material, an organic electroluminescent device, a quantum dot electroluminescent unit, and a quantum dot electroluminescent device are disclosed. The quantum dot electroluminescent unit includes a plurality of electro-phosphorescent quantum dots and at least an organic electroluminescent material, and the electro-phosphorescent quantum dots disperse in the organic electroluminescent material. The organic electroluminescent material has a structure of the following Formula (1),

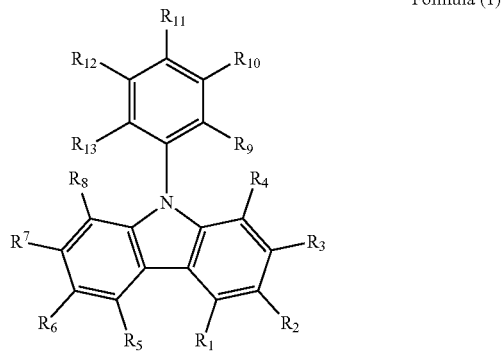

Formula (1)

wherein one or two of $R_2$, $R_4$, $R_6$, $R_9$, or $R_{13}$ are independent triazole derivatives, and the triazole derivatives have the structure of the following Formula (2), (Continued)

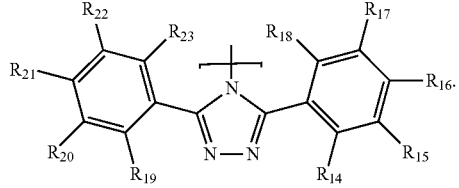

Formula (2)

19 Claims, 2 Drawing Sheets

(51) Int. Cl.
*C07D 403/10* (2006.01)
*C07D 403/14* (2006.01)
*H01L 51/50* (2006.01)

(52) U.S. Cl.
CPC .......... C09K 11/06 (2013.01); H01L 51/0067 (2013.01); *C09K 2211/1007* (2013.01); *C09K 2211/1029* (2013.01); *C09K 2211/1059* (2013.01); *H01L 51/502* (2013.01); *H01L 51/5016* (2013.01)

(56) References Cited

U.S. PATENT DOCUMENTS

2008/0286607 A1* 11/2008 Nomura .............. C07D 215/38
  428/690
2013/0146903 A1* 6/2013 Ichikawa ................ H01L 33/50
  257/88

* cited by examiner

ORGANIC ELECTROLUMINESCENT MATERIAL, ORGANIC ELECTROLUMINESCENT DEVICE AND QUANTUM DOT ELECTROLUMINESCENT UNIT

CROSS REFERENCE TO RELATED APPLICATIONS

This Non-provisional application claims priority under 35 U.S.C. § 119(a) on Patent Application No(s). 201510158326.1 and 201510158919.8 both filed in People's Republic of China on Apr. 3, 2015, the entire contents of which are hereby incorporated by reference.

BACKGROUND OF THE INVENTION

Field of Invention

The present invention relates to a luminescent material and a luminescent device and, in particular, to an organic electroluminescent material, an organic electroluminescent device and a quantum dot electroluminescent unit.

Related Art

With the advances in electronic technology, a light weight and high efficiency display device, for example an LCD (liquid crystal display) device, has been developed. However, the LCD device has some disadvantages, for example the viewing angle is not wide enough and the response time is not fast enough. Moreover, the LCD device requires polarizers and a backlight, thus increasing the power consumption, the weight and the cost.

Therefore, an organic electroluminescent display becomes the next generation flat display device due to its advantages of self-luminosity, no restriction on viewing angle, power conservation, simple manufacturing process, low cost, high response speed, full color and so on.

FIG. 1 is a schematic diagram of a conventional organic electroluminescent display. As shown in FIG. 1, the conventional organic electroluminescent device 1 includes an anode 11, a cathode 12, an organic electroluminescent layer 13 and a substrate 14. The cathode 12 can be disposed on the substrate 14, and the organic electroluminescent layer 13 includes a host material and a guest material. As to the organic electroluminescent device 1 emitting light, when a direct current is provided for the organic electroluminescent device 1, electron holes and electrons flow into the organic electroluminescent layer 13 respectively through the anode 11 and the cathode 12. Charge carriers move, meet, and then recombine in the organic electroluminescent layer 13 because of the potential difference caused by an applied electric field. The excitons generated by the recombination of the electrons and the electron holes may excite the host material to perform combination and then generate energy. The energy is then transferred to the guest material (phosphorescent material) thus generating light.

The organic electroluminescent device has a problem of insufficient color purity, the current technique utilizes a layer of quantum dot (QD) or a quantum dot complex composite material to produce a quantum dot organic electroluminescent device (QD-SOLED) to solve the problem of insufficient color purity. For example, the patent number CN101889480 discloses that a quantum dot is coated with a phosphorescent material (i.e. the above quantum dot complex composite material which is referred to as an electro-phosphorescent quantum dot in the patent application CN101889480; in order to be consistent with the term of the specification, the composite material formed by coating the quantum dot with the phosphorescent material is referred to as the electro-phosphorescent quantum dot hereafter), and then the electro-phosphorescent quantum dot is used as a guest material of an emissive layer thus to produce a quantum dot organic electroluminescent device (QD-OLED). The quantum dot organic electroluminescent device (QD-OLED) is referred to as the quantum dot electroluminescent device hereafter.

Although the quantum dot electroluminescent device may solve the problem of insufficient color purity, the host material must have fine electron and hole transport properties, and its triplet energy gap also needs to be higher than that of the guest material to avoid the energy lost caused by back energy transfer.

To make the phosphorescent material effectively work, selecting the host material is one of the key points of improving the efficiency of the components. The triplet energy gap of the selected host material must be higher than that of the guest material, so the energy may be effectively transferred. The host material itself requires semiconductor properties, i.e. having fine electron and hole transport properties. In addition, the host material also requires fine thermal stability, and then it may be possible to apply to the production line.

Currently, the organic electroluminescent devices produced by red and green guest materials mostly have fine lifespan and efficiency. However, the triplet energy gap of a blue guest material is relatively high, and the back energy transfer often results in relatively low luminous efficiency of the organic electroluminescent device. Therefore, it extremely requires a host material which meets the requirements of high triplet energy gap and sufficient thermal stability.

SUMMARY OF THE INVENTION

An organic electroluminescent material, an organic electroluminescent device having the organic electroluminescent material, and a quantum dot electroluminescent unit are provided. The organic electroluminescent material can effectively bring out the properties of the guest material (phosphorescent material) and improve the thermal stability of the host material.

The quantum dot electroluminescent unit includes quantum dots and an organic electroluminescent material. The quantum dots are coated with phosphorescent material, and they disperse in the organic electroluminescent material.

An organic electroluminescent material according to the present invention has a structure of the following Formula (1).

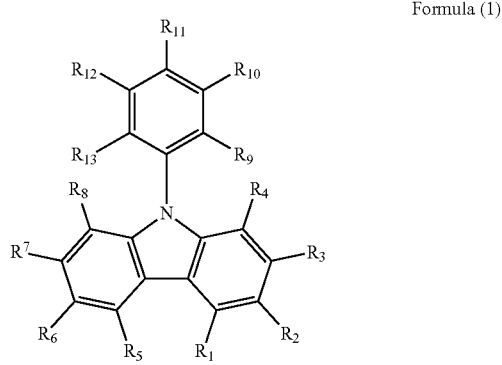

Formula (1)

One or two of $R_2$, $R_4$, $R_6$, $R_9$, or $R_{13}$ are independent triazole derivatives, and the triazole derivatives have the structure of the following Formula (2).

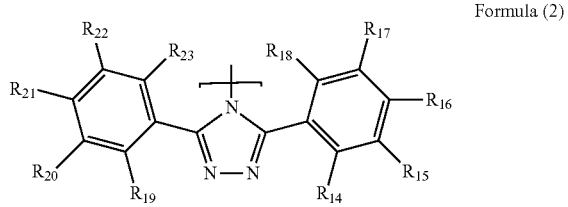

Formula (2)

The other substituents of $R_1$ to $R_{23}$ are independently selected from the group consisting of a hydrogen atom, a fluorine atom, a cyano group, an alkyl group, a cycloalkyl group, an alkoxy group, a thioalkyl group, a silyl group, and an alkenyl group.

In one embodiment, $R_1$, $R_3$, $R_5$, $R_7$, $R_8$, $R_{10}$ to $R_{12}$, and $R_{14}$ to $R_{23}$ are independently selected from the group consisting of a substituted straight-chain alkyl group with the carbon number of 1 to 6, a non-substituted straight-chain alkyl group with the carbon number of 1 to 6, a substituted branched-chain alkyl group with the carbon number of 1 to 6, a non-substituted branched-chain alkyl group with the carbon number of 1 to 6, a substituted cycloalkyl group with the carbon number of 1 to 6, a non-substituted cycloalkyl group with the carbon number of 1 to 6, a substituted straight-chain alkoxy group with the carbon number of 1 to 6, a non-substituted straight-chain alkoxy group with the carbon number of 1 to 6, a substituted branched-chain alkoxy group with the carbon number of 1 to 6, a non-substituted branched-chain alkoxy group with the carbon number of 1 to 6, a substituted straight-chain thioalkyl group with the carbon number of 1 to 6, a non-substituted straight-chain thioalkyl group with the carbon number of 1 to 6, a substituted branched-chain thioalkyl group with the carbon number of 1 to 6, a non-substituted branched-chain thioalkyl group with the carbon number of 1 to 6, a substituted straight-chain silyl group with the carbon number of 1 to 6, a non-substituted straight-chain silyl group with the carbon number of 1 to 6, a substituted branched-chain silyl group with the carbon number of 1 to 6, a non-substituted branched-chain silyl group with the carbon number of 1 to 6, a substituted straight-chain alkenyl group with the carbon number of 1 to 6, a non-substituted straight-chain alkenyl group with the carbon number of 1 to 6, a substituted branched-chain alkenyl group with the carbon number of 1 to 6, and a non-substituted branched-chain alkenyl group with the carbon number of 1 to 6.

In one embodiment, when $R_2$ is the triazole derivative, $R_1$ and $R_3$ to $R_{23}$ are independent hydrogen atoms.

In one embodiment, when $R_4$ is the triazole derivative, $R_1$ to $R_3$ and $R_5$ to $R_{23}$ are independent hydrogen atoms.

In one embodiment, when $R_9$ is the triazole derivative, $R_1$ to $R_8$ and $R_{10}$ to $R_{23}$ are independent hydrogen atoms.

In one embodiment, when $R_2$ and $R_6$ are the triazole derivatives, $R_1$, $R_3$ to $R_5$ and $R_7$ to $R_{23}$ are independent hydrogen atoms.

In one embodiment, when $R_9$ and $R_{13}$ are the triazole derivatives, $R_1$ to $R_8$, $R_{10}$ to $R_{12}$ and $R_{14}$ to $R_{23}$ are independent hydrogen atoms.

An organic electroluminescent device which is also provided includes a first electrode layer, a second electrode layer, and an organic luminescent unit. The organic luminescent unit is disposed between the first electrode layer and the second electrode layer. The organic luminescent unit has at least an organic electroluminescent material, and the organic electroluminescent material has a structure of the following Formula (1).

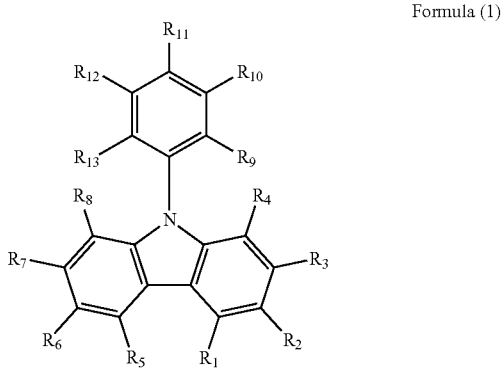

Formula (1)

One or two of $R_2$, $R_4$, $R_6$, $R_9$, or $R_{13}$ are independent triazole derivatives, and the triazole derivatives have the structure of the following Formula (2).

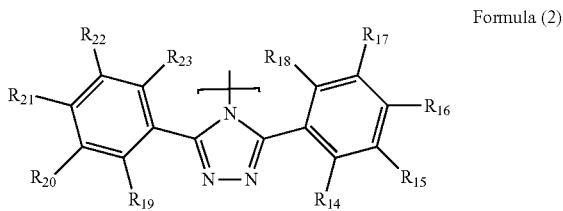

Formula (2)

The other substituents of $R_1$ to $R_{21}$ are independently selected from the group consisting of a hydrogen atom, a fluorine atom, a cyano group, an alkyl group, a cycloalkyl group, an alkoxy group, a thioalkyl group, a silyl group, and an alkenyl group.

In one embodiment, the organic electroluminescent material is selected from the group consisting of compounds of following 0-1 to 0-5:

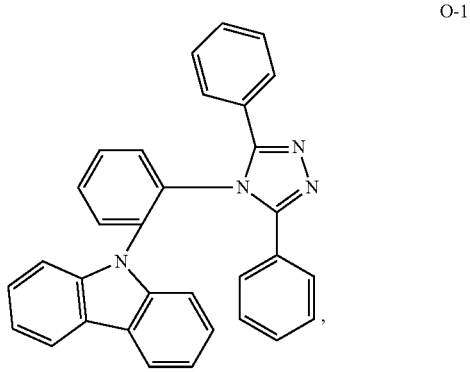

O-1

-continued

O-2
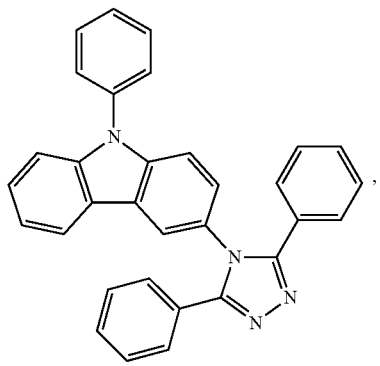,

O-3
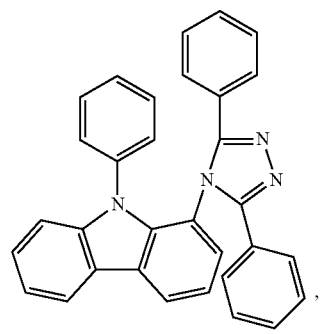,

O-4
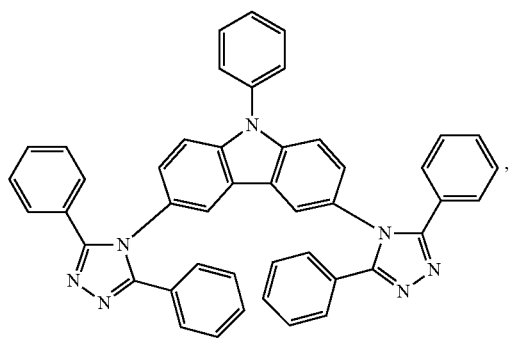, and

O-5
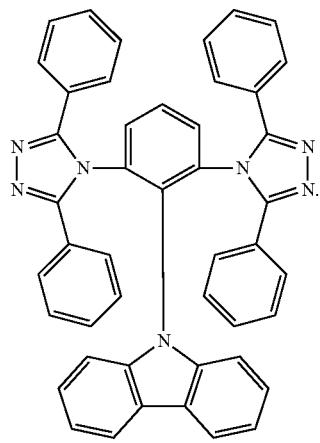

In one embodiment, the organic luminescent unit includes an organic luminescent layer, a hole transport layer and an electron transport layer, and the organic luminescent layer is disposed between the hole transport layer and the electron transport layer.

In one embodiment, the organic luminescent unit further includes an exciton blocking layer and an electron injection layer, and the exciton blocking layer, the organic luminescent layer, and the electron transport layer are in turn disposed between the hole transport layer and the electron injection layer.

In one embodiment, the organic luminescent layer includes a host material and a guest material, the host material is the organic electroluminescent material, and the guest material is a phosphorescent material.

In one embodiment, the guest material comprises one of the compounds of the following Formula (3) to (5):

Formula (3)
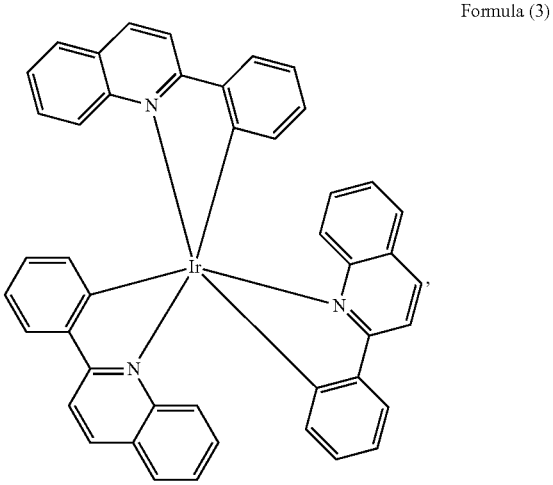,

Formula (4)
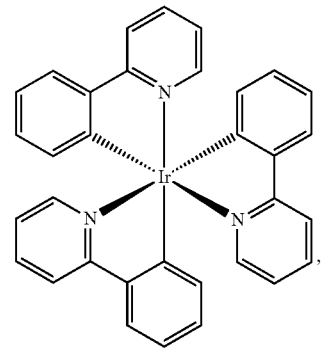,

Formula (5)
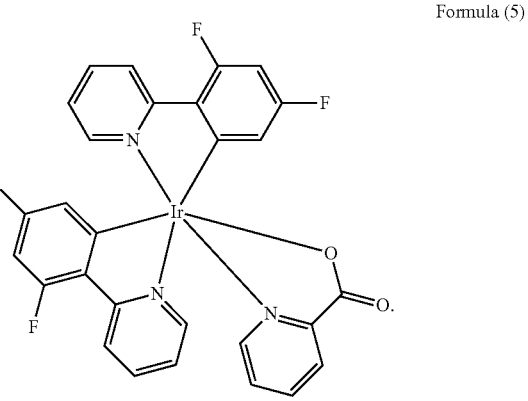.

In one embodiment, the content of the host material in the organic luminescent layer is between 60 vol % to 95 vol %.

In one embodiment, the content of the guest material in the organic luminescent layer is between 5 vol % to 40 vol %.

A quantum dot electroluminescent unit according to the present invention comprises a plurality of electro-phosphorescent quantum dots and at least an organic electroluminescent material, the electro-phosphorescent quantum dots disperse in the organic electroluminescent material, and the organic electroluminescent material has a structure of the following Formula (1).

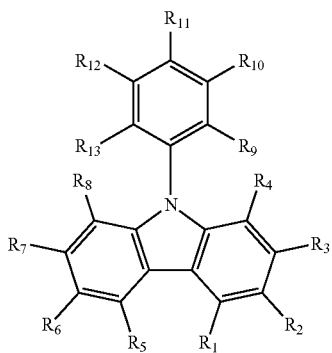

Formula (1)

One or two of $R_2$, $R_4$, $R_6$, $R_9$ or $R_{13}$ are independent triazole derivatives, and the triazole derivatives have the structures of the following Formula (2).

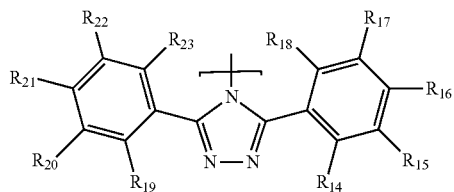

Formula (2)

The other substituents of $R_1$ to $R_{23}$ are independently selected from the group consisting of a hydrogen atom, a fluorine atom, a cyano group, an alkyl group, a cycloalkyl group, an alkoxy group, a thioalkyl group, a silyl group, and an alkenyl group.

In one embodiment, the electro-phosphorescent quantum dots are inorganic semiconductor particles coated with a phosphorescent material.

In one embodiment, the electro-phosphorescent quantum dots comprise a transition metal.

In one embodiment, the organic electroluminescent material is a host material, and the electro-phosphorescent quantum dots are a guest material.

In one embodiment, the content of the guest material in the organic electroluminescent material is between 1 vol % and 50 vol %.

As mentioned above, as to the organic electroluminescent material, the organic electroluminescent device and the quantum dot electroluminescent unit according to the present invention, the organic electroluminescent material includes the above Formula (1) and Formula (2). Compared with the conventional technique, the present invention may improve the luminous efficiency and the thermal stability of the organic electroluminescent material, the organic electroluminescent device and the quantum dot electroluminescent unit.

BRIEF DESCRIPTION OF THE DRAWINGS

The invention will become more fully understood from the detailed description and accompanying drawings, which are given for illustration only, and thus are not limitative of the present invention, and wherein.

DETAILED DESCRIPTION OF THE INVENTION

Figure 1:
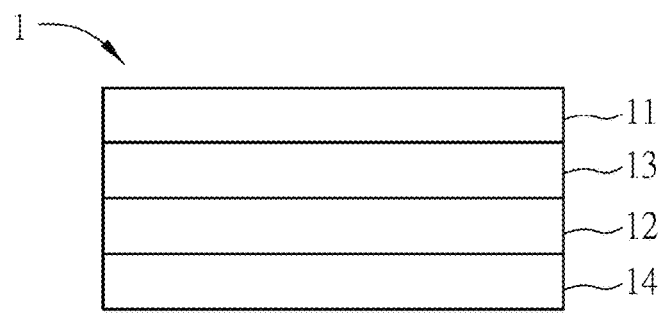
FIG. 1 is a schematic diagram of a conventional organic electroluminescent display.

The present invention will be apparent from the following detailed description, which proceeds with reference to the accompanying drawings, wherein the same references relate to the same elements.

First Embodiment

The organic electroluminescent material according to the first embodiment of the present invention has a structure of the following Formula (1).

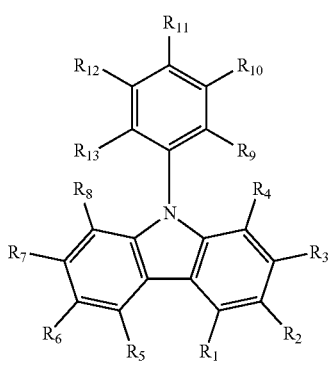

Formula (1)

The structure of above Formula (1) is a polycyclic nitrogen-containing heterocyclic compound. When $R_2$, $R_4$, $R_6$, $R_9$ and $R_{13}$ are independent hydrogen atoms, the structure of Formula (1) is N-phenyl carbazole (NPC) which belongs to a carbazole derivative also known as a carbazolyl group. In the embodiment, one or two of $R_2$, $R_4$, $R_6$, $R_9$ or $R_{13}$ may be independent triazole derivatives. The triazole derivative of the embodiment is a derivative having the structure of the following Formula (2).

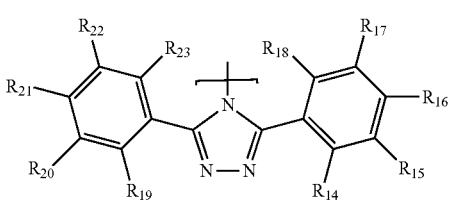

Formula (2)

Namely in the embodiment, a nitrogen atom of the triazole derivative is used to attach to one or two of $R_2$, $R_4$, $R_6$, $R_9$ or $R_{13}$ of N-phenyl carbazole to form a double dipole molecule of high triplet energy state, i.e. the organic electroluminescent material of the embodiment. When one or two of $R_2$, $R_4$, $R_6$, $R_9$ or $R_{13}$ are triazole derivatives, other substituents may be one or more hydrogen atom, fluorine atom, cyano group, alkyl group, cycloalkyl group, alkoxy group, thioalkyl group, silyl group, or alkenyl group, and the present invention is not limited thereto.

In detail, when $R_2$ is the triazole derivative, $R_1$ and $R_3$ to $R_{23}$ are independently selected from the group consisting of a hydrogen atom, a fluorine atom, a cyano group, an alkyl group, a cycloalkyl group, an alkoxy group, a thioalkyl group, a silyl group, and an alkenyl group; when $R_4$ is the triazole derivative, $R_1$ to $R_3$ and $R_5$ to $R_{23}$ are independently selected from the group consisting of a hydrogen atom, a fluorine atom, a cyano group, an alkyl group, a cycloalkyl group, an alkoxy group, a thioalkyl group, a silyl group, and an alkenyl group; when $R_6$ is the triazole derivative, $R_1$ to $R_5$ and $R_7$ to $R_{23}$ are independently selected from the group consisting of a hydrogen atom, a fluorine atom, a cyano group, an alkyl group, a cycloalkyl group, an alkoxy group, a thioalkyl group, a silyl group, and an alkenyl group; when $R_9$ is the triazole derivative, $R_1$ to $R_8$ and $R_{10}$ to $R_{23}$ are independently selected from the group consisting of a hydrogen atom, a fluorine atom, a cyano group, an alkyl group, a cycloalkyl group, an alkoxy group, a thioalkyl group, a silyl group, and an alkenyl group; when $R_{13}$ is the triazole derivative, $R_1$ to $R_{12}$, and $R_{14}$ to $R_{23}$ are independently selected from the group consisting of a hydrogen atom, a fluorine atom, a cyano group, an alkyl group, a cycloalkyl group, an alkoxy group, a thioalkyl group, a silyl group, and an alkenyl group; when $R_2$ and $R_4$ are the triazole derivatives, $R_1$, $R_3$ and $R_5$ to $R_{23}$ are independently selected from the group consisting of a hydrogen atom, a fluorine atom, a cyano group, an alkyl group, a cycloalkyl group, an alkoxy group, a thioalkyl group, a silyl group, and an alkenyl group; when $R_2$ and $R_6$ are the triazole derivatives, $R_1$, $R_3$ to $R_5$ and $R_7$ to $R_{23}$ are independently selected from the group consisting of a hydrogen atom, a fluorine atom, a cyano group, an alkyl group, a cycloalkyl group, an alkoxy group, a thioalkyl group, a silyl group, and an alkenyl group; when $R_2$ and $R_9$ are the triazole derivatives, $R_1$, $R_3$ to $R_8$ and $R_{10}$ to $R_{23}$ are independently selected from the group consisting of a hydrogen atom, a fluorine atom, a cyano group, an alkyl group, a cycloalkyl group, an alkoxy group, a thioalkyl group, a silyl group, and an alkenyl group; when $R_2$ and $R_{13}$ are the triazole derivatives, $R_1$, $R_3$ to $R_{12}$ and $R_{14}$ to $R_{23}$ are independently selected from the group consisting of a hydrogen atom, a fluorine atom, a cyano group, an alkyl group, a cycloalkyl group, an alkoxy group, a thioalkyl group, a silyl group, and an alkenyl group; when $R_4$ and $R_6$ are the triazole derivatives, $R_1$ to $R_3$, $R_5$, and $R_7$ to $R_{23}$ are independently selected from the group consisting of a hydrogen atom, a fluorine atom, a cyano group, an alkyl group, a cycloalkyl group, an alkoxy group, a thioalkyl group, a silyl group, and an alkenyl group; when $R_4$ and $R_9$ are the triazole derivatives, $R_1$ to $R_3$, $R_5$ to $R_8$, and $R_{10}$ to $R_{23}$ are independently selected from the group consisting of a hydrogen atom, a fluorine atom, a cyano group, an alkyl group, a cycloalkyl group, an alkoxy group, a thioalkyl group, a silyl group, and an alkenyl group; when $R_4$ and $R_{13}$ are the triazole derivatives, $R_1$ to $R_3$, $R_5$ to $R_{12}$, and $R_{14}$ to $R_{23}$ are independently selected from the group consisting of a hydrogen atom, a fluorine atom, a cyano group, an alkyl group, a cycloalkyl group, an alkoxy group, a thioalkyl group, a silyl group, and an alkenyl group; when $R_6$ and $R_9$ are the triazole derivatives, $R_1$ to $R_5$, $R_7$ to $R_8$, and $R_{10}$ to $R_{23}$ are independently selected from the group consisting of a hydrogen atom, a fluorine atom, a cyano group, an alkyl group, a cycloalkyl group, an alkoxy group, a thioalkyl group, a silyl group, and an alkenyl group; when $R_6$ and $R_{13}$ are the triazole derivatives, $R_1$ to $R_5$, $R_7$ to $R_{12}$, and $R_{14}$ to $R_{23}$ are independently selected from the group consisting of a hydrogen atom, a fluorine atom, a cyano group, an alkyl group, a cycloalkyl group, an alkoxy group, a thioalkyl group, a silyl group, and an alkenyl group; when $R_9$ and $R_{13}$ are the triazole derivatives, $R_1$ to $R_8$, $R_{10}$ to $R_{12}$ and $R_{14}$ to $R_{23}$ are independently selected from the group consisting of a hydrogen atom, a fluorine atom, a cyano group, an alkyl group, a cycloalkyl group, an alkoxy group, a thioalkyl group, a silyl group, and an alkenyl group.

In the embodiment, an alkyl group may be a substituted straight-chain alkyl group with the carbon number of 1 to 6, a non-substituted straight-chain alkyl group with the carbon number of 1 to 6, a substituted branched-chain alkyl group with the carbon number of 1 to 6, or a non-substituted branched-chain alkyl group with the carbon number of 1 to 6. A cycloalkyl group may be a substituted cycloalkyl group with the carbon number of 1 to 6 or a non-substituted cycloalkyl group with the carbon number of 1 to 6. An alkoxy group may be a substituted straight-chain alkoxy group with the carbon number of 1 to 6, a non-substituted straight-chain alkoxy group with the carbon number of 1 to 6, a substituted branched-chain alkoxy group with the carbon number of 1 to 6, or a non-substituted branched-chain alkoxy group with the carbon number of 1 to 6. A thioalkyl group may be a substituted straight-chain thioalkyl group with the carbon number of 1 to 6, a non-substituted straight-chain thioalkyl group with the carbon number of 1 to 6, a substituted branched-chain thioalkyl group with the carbon number of 1 to 6, or a non-substituted branched-chain thioalkyl group with the carbon number of 1 to 6. A silyl group may be a substituted straight-chain silyl group with the carbon number of 1 to 6, a non-substituted straight-chain silyl group with the carbon number of 1 to 6, a substituted branched-chain silyl group with the carbon number of 1 to 6, or a non-substituted branched-chain silyl group with the carbon number of 1 to 6. An alkenyl group may be a substituted straight-chain alkenyl group with the carbon number of 1 to 6, a non-substituted straight-chain alkenyl group with the carbon number of 1 to 6, a substituted branched-chain alkenyl group with the carbon number of 1 to 6, or a non-substituted branched-chain alkenyl group with the carbon number of 1 to 6, and the present invention is not limited thereto.

For example, the organic electroluminescent material according to the embodiment may be the compounds having the following structural formulas:

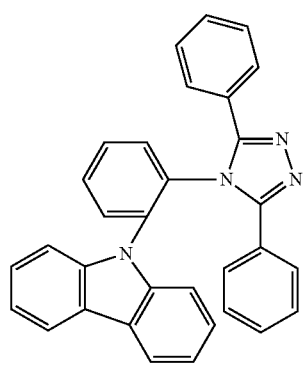

O-1

-continued

O-2
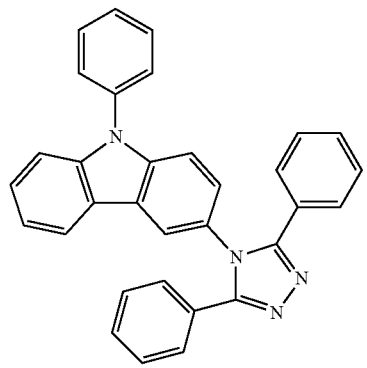

O-3
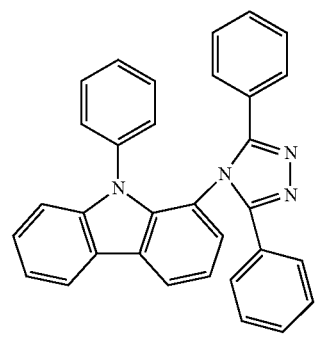

O-4
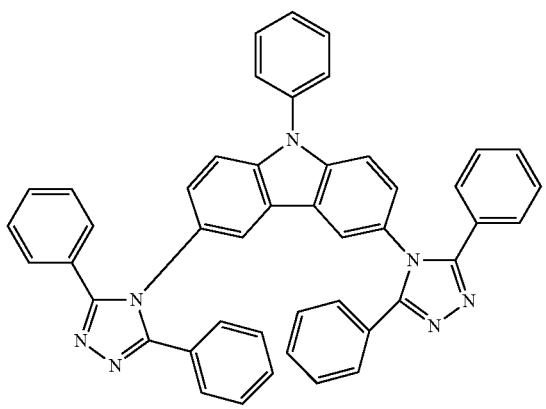

O-5
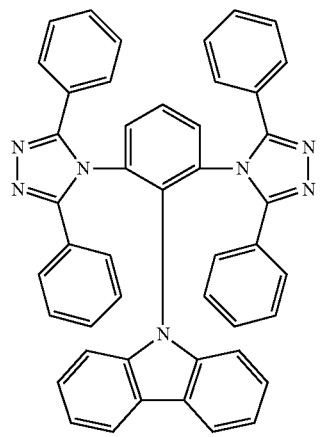

Here, Compound O-1 is a structural formula that $R_1$ to $R_8$ and $R_{10}$ to $R_{23}$ are independent hydrogen atoms when $R_9$ is the triazole derivative. Compound O-2 is a structural formula that $R_1$ and $R_3$ to $R_{23}$ are independent hydrogen atoms when $R_2$ is the triazole derivative. Compound O-3 is a structural formula that $R_1$ to $R_3$ and $R_5$ to $R_{23}$ are independent hydrogen atoms when $R_4$ is the triazole derivative. Compound O-4 is a structural formula that $R_1$, $R_3$ to $R_5$ and $R_7$ to $R_{23}$ are independent hydrogen atoms when $R_2$ and $R_6$ are the triazole derivatives. Compound O-5 is a structural formula that $R_1$ to $R_8$, $R_{10}$ to $R_{12}$ and $R_{14}$ to $R_{23}$ are independent hydrogen atoms when $R_9$ and $R_{13}$ are the triazole derivatives.

As described above, the organic electroluminescent material of the embodiment is a carbazole derivative in which by ortho-substitution in the benzene ring, two aromatic groups are staggered in space due to steric hindrance. Namely, the carbazolyl group (compound of Formula (1)) and the triazole group (compound of Formula (2)) are staggered in space so as to reduce the conjugated system of the whole molecule. It results in that the organic electroluminescent material has the relatively high triplet energy gap and the structure of the multiple benzene rings of the carbazole derivative has excellent thermal stability.

Second Embodiment

Figure 2:
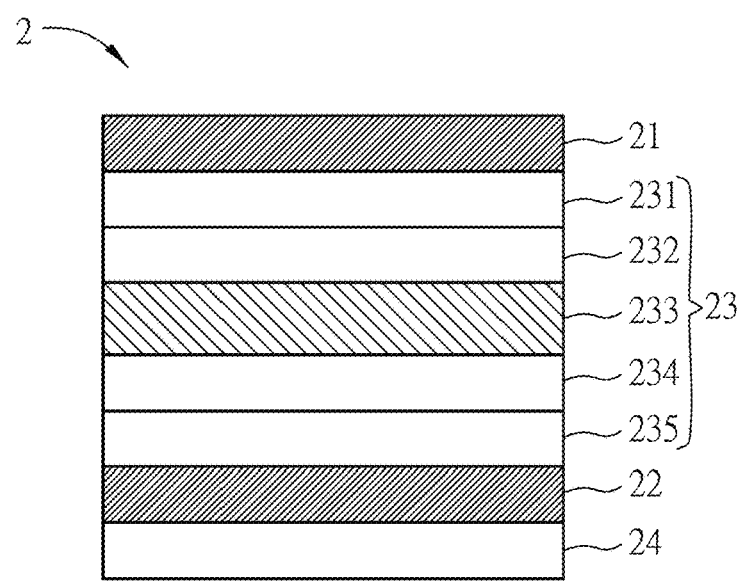
FIG. 2 is a schematic diagram of an organic electroluminescent device of the second embodiment according to the invention.

Referring to FIG. 2, it is a schematic diagram of an organic electroluminescent device of the second embodiment according to the invention. The organic electroluminescent device 2 of the embodiment includes a first electrode layer 21, a second electrode layer 22, and an organic luminescent unit 23. The organic luminescent unit 23 is disposed between the first electrode layer 21 and the second electrode layer 22. The organic luminescent unit 23 has at least an organic electroluminescent material, and the organic electroluminescent material is the organic electroluminescent material (carbazole derivative) described in the first embodiment. Therefore, the details may refer to the description of the first embodiment, and they are not repeated here.

In the embodiment, the first electrode layer 21 is disposed on the substrate 24, and the substrate 24 is selected from at least one of a rigid substrate, a flexible substrate, a glass substrate, a plastic substrate, and a silicon substrate. The flexible substrate and the plastic substrate may be polycarbonate (PC) substrates, polyester (PET) substrates, cyclic olefin copolymer (COC) substrates, metallocene-based cyclic olefin copolymer (mCOC) substrates, polymethylmethacrylate substrates, polymer substrates, and so on. The first electrode layer 21 may be formed on the substrate 24 by sputtering or ion plating. The first electrode layer 21 often acts as an anode and its material is generally a transparent electrode material, such as indium tin oxide (ITO), aluminum zinc oxide (AZO), or indium zinc oxide (IZO) and the like. Moreover, the second electrode layer 22 may be a conductive substance. For example, its material may be selected from at least one of aluminum, calcium, magnesium, indium, tin, manganese, copper, silver, gold and alloys thereof. The magnesium-containing alloy is such as a magnesium-silver alloy, a magnesium-indium alloy, a magnesium-tin alloy, a magnesium-antimony alloy and a magnesium-tellurium alloy. In the embodiment, the first electrode layer 21 is a transparent electrode material, and the second electrode layer 22 may, for example, be a metal. Furthermore, the materials and functions as the anode or the cathode of the first electrode layer 21 and the second electrode layer 22 may be interchanged dependent on practical needs. Overall, at least one of the first electrode layer 21 or the second electrode layer 22 of the embodiment is a transparent electrode material, so that the light emitted from the organic luminescent unit 23 may pass through the transparent electrode, thereby enabling the organic electroluminescent device 2 to emit light.

In the embodiment, the organic luminescent unit 23 is formed on the first electrode layer 21 by, for example, evaporation, molecular beam epitaxy (MBE), immersion, spin coating, casting, roll coating, printing, ink jet printing, transfer, etc. Alternatively, the second electrode layer 22 is disposed on the organic luminescent unit 23. Here, the second electrode layer 22 may be formed on the organic luminescent unit 23 by evaporation or sputtering, etc.

Preferably, the organic luminescent unit 23 of the embodiment further includes a hole transport layer 231, an exciton blocking layer 232, an organic luminescent layer 233, an electron transport layer 234, and an electron injection layer 235. As shown in FIG. 2, the hole transport layer 231, the exciton blocking layer 232, the organic luminescent layer 233, the electron transport layer 234, and the electron injection layer 235 are in turn disposed between the first electrode layer 21 and the second electrode layer 22. In other words, the hole transport layer 231 and the electron injection layer 235 are respectively connected to the first electrode layer 21 and the second electrode layer 22. The exciton blocking layer 232, the organic luminescent layer 233, and the electron transport layer 234 are in turn disposed between the hole transport layer 231 and the electron injection layer 235. In other embodiments, the organic luminescent unit may also be a structure consisting of the hole transport layer, the organic luminescent layer, and the electron transport layer, and the organic luminescent layer is disposed between the hole transport layer and the electron transport layer.

In the embodiment, the hole transport layer 231 is disposed between the first electrode layer 21 and the exciton blocking layer 232. The material of the hole transport layer 231 may be composed of any material of triphenylamine, such as 4,4'-bis[N-(1-naphthyl)-N-phenylamino]bipheny (NPB) or 3-tryptimino-1-phenyl-butan-1-one (TPB). Moreover, the thickness of the hole transport layer 231 of the embodiment is in the range of, for example, 0.1 nm to 100 nm. The hole transport layer 231 may facilitate the electron hole to be transported from the first electrode layer 21 to the organic luminescent layer 233 in order to increase the transport rate of the electron hole.

The exciton blocking layer 232 is disposed between the hole transport layer 231 and the organic luminescent layer 233. Here, the material of the exciton blocking layer 232 is, for example, 1,3-bis(carbazol-9-yl)benzene (mCP) or other materials with the high triplet energy gap. In the embodiment, the thickness of the exciton blocking layer 232 is in the range of, for example, 0.1 nm to 30 nm. The exciton blocking layer 232 may prevent the exciton from diffusing from the organic luminescent layer 233 to proximity to the first electrode layer 21 and thus to quench.

The organic luminescent layer 233 is disposed between the exciton blocking layer 232 and electron transport layer 234. The thickness of the organic luminescent layer 233 of the embodiment is between 5 nm and 60 nm, the organic luminescent layer 233 includes the host material and the guest material, and the host material can be the above mentioned organic electroluminescent material, i.e. the organic electroluminescent material described in the first embodiment (carbazole derivative). Preferably, the organic electroluminescent material is one of aforementioned Compound O-1 to Compound O-5 or any combination thereof, and it is not limited thereto. The guest material of the embodiment is the phosphorescent material. Moreover, it may be any luminescent material applied to the organic luminescent layer of the organic electroluminescent device, for example but not limited to, Ir(2-phq)$_3$, Ir(ppy)$_3$, and FIrpic, and their structures are respectively shown as the following Formula (3), Formula (4), and Formula (5).

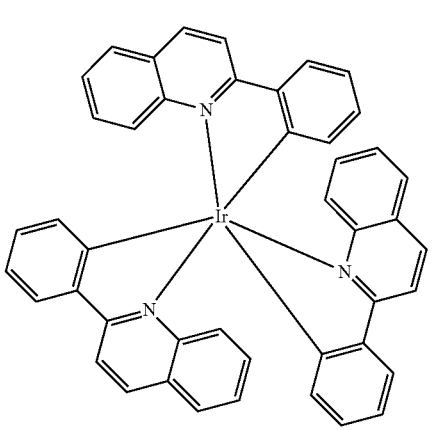

Formula (3)

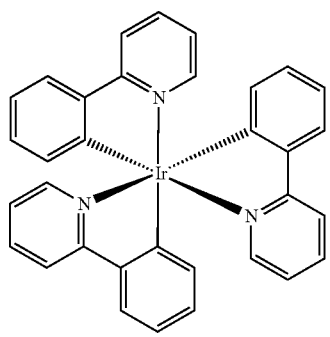

Formula (4)

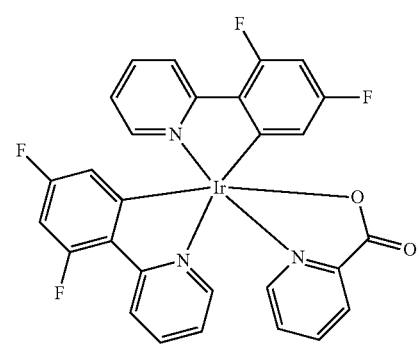

Formula (5)

Preferably, the content of the host material of the embodiment in the organic luminescent layer 233 is between 60 vol % and 95 vol %, and that of the guest material in the organic luminescent layer 233 is between 5 vol % and 40 vol %.

The electron transport layer 234 of the embodiment is disposed between the organic luminescent layer 233 and the electron injection layer 235. The material of the electron transport layer 234 may be, for example but not limited to, a metal complex such as AR) and BeBq2 or a heterocyclic compound such as PBD, TAZ, TPBI, and DPPS. In the embodiment, the thickness of the electron transport layer 234 may be between 0.1 nm and 100 nm. The electron transport layer 234 may improve the velocity of the electron being transported from the electron injection layer 235 to the organic luminescent layer 233.

Alternatively, in addition to acting as the host material of the organic luminescent layer 233, the organic electroluminescent material of the embodiment may be used for other layers of the organic luminescent unit 23, such as the hole transport layer 231, the exciton blocking layer 232, the electron transport layer 234, and the electron injection layer 235. In other embodiments, when the organic luminescent unit has a hole injection layer and a hole blocking layer, the organic electroluminescent material of the embodiment may be also applied to such layers, and it is not limited thereto.

In the organic electroluminescent device 2, in order to improve the luminous efficiency of the organic luminescent layer 233, the triplet energy gap of the host material has to be higher than that of the guest material to avoid the decrease of the luminous efficiency of the organic electroluminescent device caused by back energy transfer. In the embodiment, the organic electroluminescent material (carbazole derivative) acts as the host material, and it may have the relatively high triplet energy gap and thus avoid back energy transfer from the guest material so as to improve the luminous efficiency of the organic electroluminescent device.

In order to make the above mentioned embodiments more easily be understood, the following examples illustrate the synthesis methods for the organic electroluminescent material and the manufacturing process of the organic electroluminescent device.

Example 1: Synthesis of Compound O-1

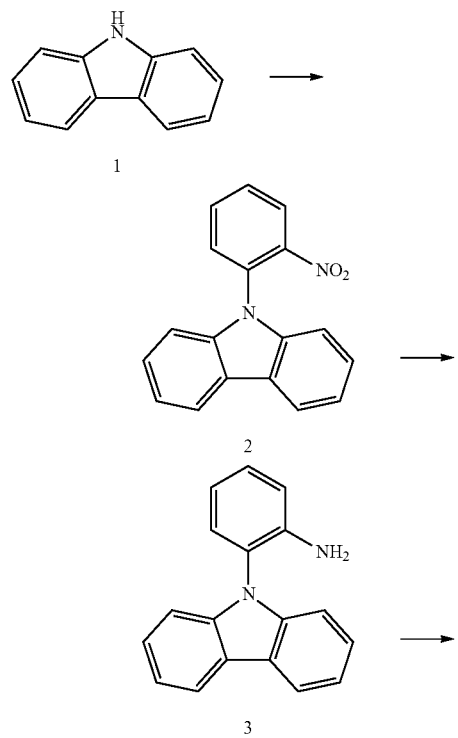

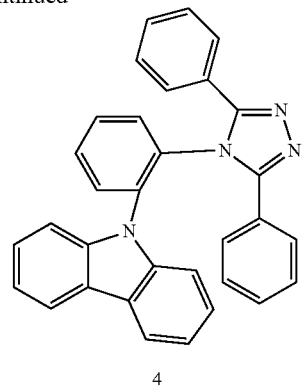

Carbazole (i.e. Compound 1, 0.30 g, 1.8 mmol), 1-fluoro-3-nitrobenzene (0.25 g, 1.8 mmol), and dimethylsulfoxide (5 mL) are placed into a single neck flask (10 mL) After stirred with a magnetic stir bar until solids dissolve followed by adding cesium carbonate (0.64 g, 2.0 mmol), they react at room temperature for 18 hours. Next, after deionized water (5 mL) is added, a yellow solid is generated. It is then extracted with trichloromethane (30 mL) for three times. The organic layer is collected and then washed with deionized water (30 mL) for three times. After the organic layer is dried over anhydrous magnesium sulfate, the solvent is removed by a rotary concentration to obtain Compound 2 (0.49 g), and the yield is 94%.

Then, Compound 2 (2.0 g, 6.9 mmol), tin(II) chloride dihydrate (7.83 g, 34.7 mmol), ethyl acetate (34.5 mL), and ethanol (34.5 mL) are placed into a single neck flask (250 mL) and stirred with a magnetic stir bar. Subsequently, the erected condenser is heated to 90° C. and refluxed for 10 hours. After the solution cools to room temperature, it is poured into 2 M aqueous solution of potassium hydroxide and then extracted with ethyl acetate to collect the organic layer. After the organic layer is dried over anhydrous magnesium sulfate, the solvent is removed by a rotary concentration to obtain Compound 3 (1.77 g), and the yield is 99%.

Finally, Compound 3 (0.32 g, 1.2 mmol), N-(chloro(phenyl)methylene) benzohydrazonoyl chloride (0.34 g, 1.2 mmol), triethylamine (0.35 mL, 2.4 mmol), N,N-dimethylforamide (0.19 mL, 2.4 mmol), and p-xylene (12 mL) are placed into a single neck flask (25 mL) and stirred with a magnetic stir bar. The condenser is erected, heated to 160° C. and refluxed for 34 hours. Subsequently, the solvent is removed by vacuum distillation. After the mixture is heated and stirred with acetone for several hours, the white solid is separated out by suction filtration. Last, dichloromethane and ethanol are further used for recrystallization to obtain Compound 4, i.e. Compound O-1 (0.24 g), and the yield is 42%.

Spectral data as follow: $^1$H NMR (400 MHz, CD$_2$Cl$_2$) δ7.94 (d, J=7.8 Hz, 2H), 7.91-7.89 (m, 1H), 7.77-7.70 (m, 2H), 7.56-7.53 (m, 1H), 7.28 (tt, J=7.2 Hz, 1.4 Hz, 2H), 7.24-7.22 (m, 4H), 7.19-7.15 (m, 4H), 7.11 (t, J=7.8 Hz, 2H), 6.91-6.87 (2H), 6.35 (d, J=8.3 Hz, 2H); $^{13}$C NMR (100 MHz, CDCl$_3$) δ154.32, 140.22, 135.01, 132.82, 131.91, 131.75, 131.42, 129.90, 128.92, 128.55, 128.44, 126.87, 125.97, 123.66, 120.35, 119.94, 109.27. HRMS (EI) m/z calcd for C$_{32}$H$_{22}$N$_4$ 462.1839, obsd. 462.1838. Anal. Calcd for C$_{32}$H$_{22}$N$_4$: C, 83.09; H, 4.79; N, 12.11. Found: C, 82.96; H, 4.79; N, 12.10.

Example 2: Synthesis of Compound O-2

Compound 6: 3-nitro-9-phenyl-9H-carbazole

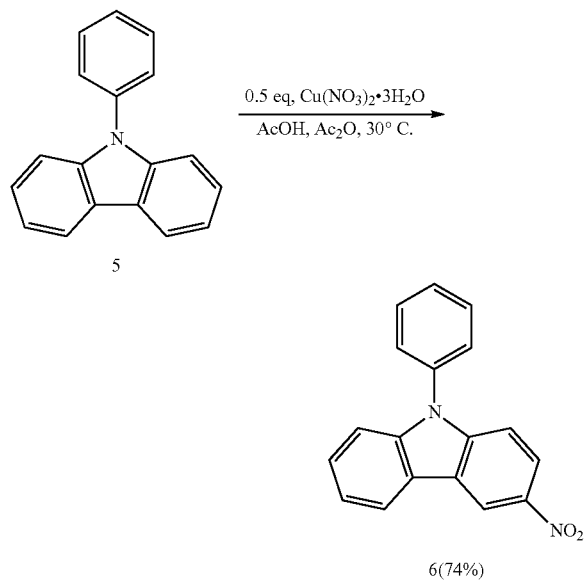

6(74%)

Compound 5 (i.e. copper nitrate trihydrate, 0.99 g, 4.1 mmol), acetic acid (7.5 mL), and acetic anhydride (12.5 mL) are placed into a single neck flask (100 mL) and stirred with a magnetic stir bar for 10 minutes. 9-phenylcarbazole (2.00 g, 8.22 mmol) is added and then stirred in water bath at 30° C. for 30 minutes. Subsequently, deionized water (50 mL) is added to yield a yellow solid. The solid is collected by suction filtration and washed with deionized water several times. Then, the solid is stirred and washed with acetonitrile. After suction filtration, the obtained bright yellow solid is Compound 6 (1.74 g), and the yield is 74%.

Spectral data as follow: 1H NMR (400 MHz, CDCl3) δ9.04 (d, J=2.4 Hz, 1H), 8.30 (dd, J=8.0 Hz, 4.0 Hz, 1H), 8.18 (d, J=8.0 Hz, 1H), 7.62 (t, J=8.0 Hz, 2H), 7.51-7.47 (m, 4H), 7.40-7.24 (m, 3H): 13C NMR (100 MHz, CDCl3) δ144.13, 142.53, 141.57, 136.51, 130.46, 128.85, 127.83, 127.31, 123.27, 123.17, 121.99, 121.77, 121.09, 117.4, 110.88, 109.70.

Compound 7: 9-phenyl-9H-carbazol-3-amine

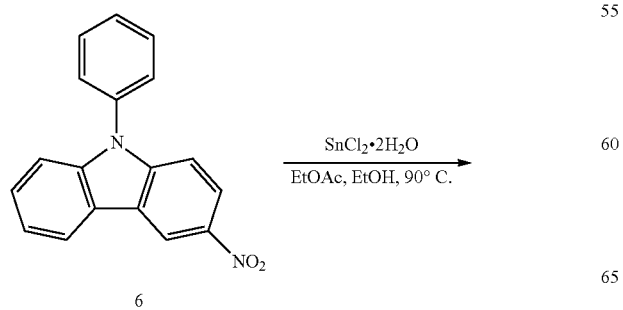

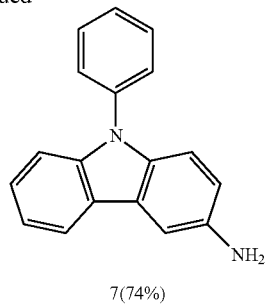

7(74%)

Compound 6 (1.55 g, 5.38 mmol), tin(II) chloride dihydrate (6.07 g, 26.9 mmol), ethyl acetate (27 mL), and ethanol (27 mL) are placed into a single neck flask (100 mL) and stirred with a magnetic stir bar. Moreover, the erected condenser is heated to 90° C. and refluxed for 10 hours. After the solution cools to room temperature, it is poured into 2 M aqueous solution of potassium hydroxide and then extracted with ethyl acetate to collect the organic layer. After the organic layer is dried over anhydrous magnesium sulfate, the solvent is removed by a rotary concentration to obtain a red viscous product 9-phenyl-9H-carbazol-3-amine, i.e. Compound 7 (1.57 g).

Spectral data as follow: 1H NMR (400 MHz, d6-DMSO) δ8.02 (d, J=7.6 Hz, 1H), 7.64 (t, J=8 Hz, 2H), 7.57 (d, J=7.6 Hz, 2H), 7.46 (t, J=7.2 Hz, 1H), 7.34 (d, J=3.2 Hz, 3H), 7.19-7.14 (m, 2H), 6.79 (dd, J=8.8 Hz, 2.0 Hz, 1H), 4.87 (s, 2H); 13C NMR (100 MHz, d6-DMSO) δ142.75, 140.11, 137.55, 133.05, 130.01, 126.85, 126.16, 125.62, 123.52, 122.69, 120.16, 119.17, 115.31, 109.98, 109.31, 103.80.

Compound 8 (i.e. Compound O-2): 3-(3,5-diphenyl-4H-1,2,4-triazol-4-yl)-9-phenyl-9H-carbazole

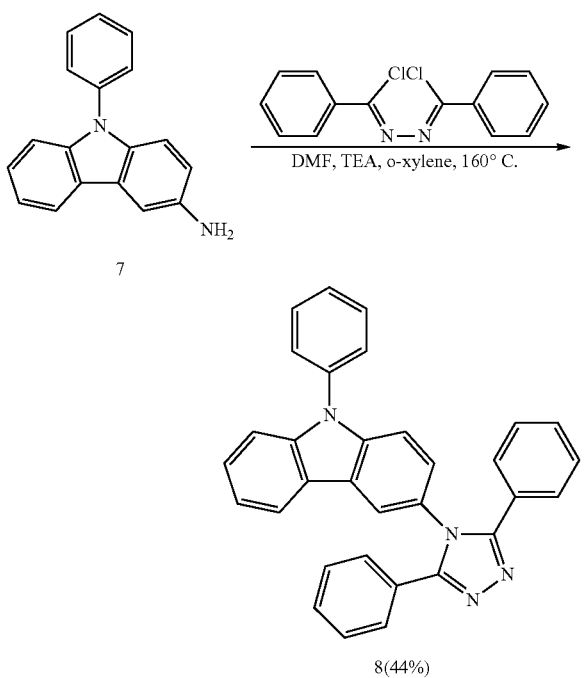

8(44%)

Compound 7 (1.57 g, 6.08 mmol), N'-(chloro(phenyl)methylene) benzohydrazonoyl chloride (1.68 g, 6.08 mmol), triethylamine (1.70 mL, 12.2 mmol), N,N-dimethylforamide (0.94 mL, 12 mmol), and p-xylene (60 mL) are placed into a single neck flask (100 mL) and stirred with a magnetic stir bar. The erected condenser is heated to 160° C. and refluxed for 5 days. Subsequently, the solvent is removed by vacuum distillation. After the mixture is heated and stirred with acetone for several hours, the solid is collected by suction filtration. Then, dichloromethane and ethanol are used for recrystallization to obtain a reddish brown crystal. After the reddish brown crystal sublimates, a white solid (i.e. Compound 8, 1.23 g) is obtained, and the yield is 44%. In addition, Compound 8 synthesized in the embodiment is 3-(3,5-diphenyl-4H-1,2,4-triazol-4-yl)-9-phenyl-9H-carbazole, i.e. Compound O-2.

Spectral data as follow: mp. 291° C. 1H NMR (400 MHz, CD2Cl2) δ8.02 (d, J=7.7 Hz, 1H), 7.97 (d, J=2.0 Hz, 1H), 7.67-7.63 (m, 2H), 7.61-7.59 (m, 2H), 7.55-7.42 (m, 8H), 7.34-7.21 (m, 8H); 13C NMR (100 MHz, CDCl3) δ155.50, 141.92, 140.80, 137.03, 130.31, 129.64, 128.60, 128.35, 127.64, 127.49, 127.40, 127.26, 125.52, 124.22, 122.68, 121.01, 120.86, 119.94, 111.04, 110.59. HRMS (EI) m/z calcd for C32H22N4 462.1839, obsd. 462.1839. Anal. Calcd for $C_{32}H_{22}N_4$: C, 83.09; H, 4.79; N, 12.11. Found: C, 83.27; H, 4.90; N, 12.06.

Example 3: Synthesis of Compound O-3

Compound 9: 1-nitro-9H-carbazole

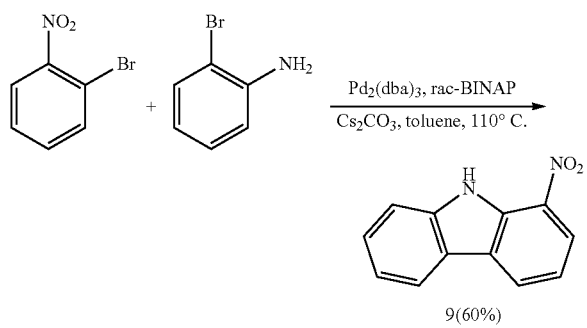

9(60%)

2-bromoaniline (0.43 g, 2.5 mmol), 1-bromo-2-nitrobenzene (0.52 g, 2.5 mmol), tris(dibenzylideneacetone)dipalladium(0) (0.114 g, 0.125 mmol), rac-2,2'-Bis(diphenylphosphino)-1,1'-binaphthyl (0.117 g, 0.188 mmol), and cesium carbonate (1.63 g, 5.00 mmol) are placed into a two neck flask (10 mL) and stirred with a magnetic stir bar. After argon is swapped several times in the erected condenser, toluene (5 mL) is injected, and then it is heated to 110° C. and reacted for 20 hours. After the mixture cools to room temperature, it is filtered by diatomaceous earth to collect the filtrate. After rotary concentration, the column chromatography is performed with the eluent (ethyl acetate:n-hexane=1:12) to obtain Compound 9 (0.32 g, a yellow solid), the yield is 60%.

Spectral data as follow: 1H NMR (400 MHz, d6-DMSO) δ12.17 (s, 1H), 8.62 (dd, J=7.6 Hz, 0.8, 1H), 8.31 (d, J=8.0 Hz, 1H), 8.25 (d, J=7.6 Hz, 1H), 7.75 (dd, J=8.0 Hz, 0.8 Hz, 1H), 7.51 (t, J=8.0 Hz, 1H), 7.36 (t, J=7.6 Hz, 1H), 7.30 (t, J=7.6 Hz, 1H); 13C NMR (100 MHz, d6-DMSO) δ140.42, 132.68, 131.45, 127.86, 127.12, 126.91, 121.51, 121.31, 120.50, 120.43, 118.14, 112.45.

Compound 10: 1-nitro-9-phenyl-9H-carbazole

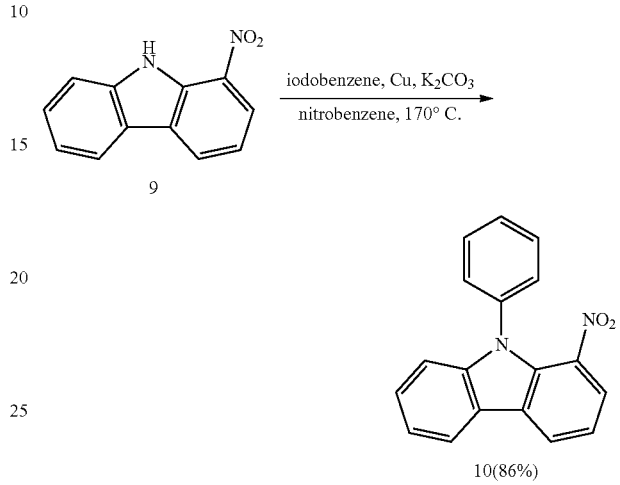

10(86%)

Compound 9 (1.00 g, 4.71 mmol), iodobenzene (1.44 g, 7.06 mmol), copper (0.30 g, 4.7 mmol), potassium carbonate (1.30 g, 9.41 mmol), and nitrobenzene (7.8 mL) are placed into a single neck flask (25 mL), and the erected condenser is heated to 180° C. and reacted for 3 days. After the mixture cools to room temperature, it is filtered by diatomaceous earth to collect the filtrate. After rotary concentration, the column chromatography is performed with the eluent (dichloromethane:n-hexane=1:2) to obtain an orange solid. Subsequently, n-hexane is further used for recrystallization to obtain Compound 10 (1.17 g, a yellow needle solid), and the yield is 86%.

Structure identification data as follow: 1H NMR (400 MHz. CDCl3) δ 8.37 (dd, J=7.6, 1.2, 1H), 8.14 (d, J=7.6, 1H), 7.97 (dd, J=8.0, 0.8, 1H), 7.54 (tt, J=8.0, 1.2, 2H), 7.47-7.44 (m, 2H), 7.38-7.30 (m, 5H); 13C NMR (100 MHz, CDCl3) δ 143.20, 138.47, 135.69, 132.15, 129.78, 128.36, 128.28, 127.70, 126.03, 125.32, 122.62, 122.27, 121.70, 120.37, 119.30, 111.12.

Compound 11: 9-phenyl-9H-carbazol-1-amine

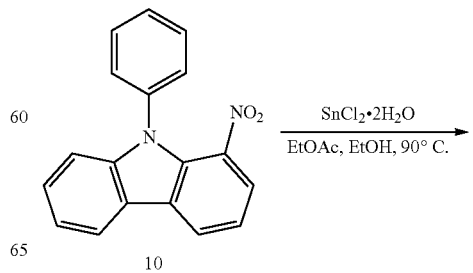

10

-continued

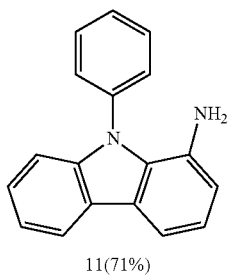

11(71%)

Compound 10 (0.50 g, 1.7 mmol), tin(II) chloride dihydrate (1.96 g, 8.69 mmol), ethyl acetate (8.6 mL), and ethanol (8.6 mL) are placed into a single neck flask (25 mL) and stirred with a magnetic stir bar. Subsequently, the erected condenser is heated to 90° C. and refluxed for 10 hours. After the mixture cools to room temperature, it is poured into 2 M aqueous solution of potassium hydroxide and then extracted with ethyl acetate to collect the organic layer. The organic layer is dried over anhydrous magnesium sulfate and then the solvent is removed by a rotary concentration to obtain a dark green viscous product. Then, the column chromatography is performed with the eluent (dichloromethane:n-hexane=1:1) to obtain Compound 11 (0.32 g, a purplish black viscous product), and the yield is 71%.

Spectral data as follow: 1H NMR (400 MHz, d6-DMSO) δ8.11 (d, J=7.6 Hz, 1H), 7.64 (t, J=7.6 Hz, 2H), 7.58 (d, J=7.2 Hz, 1H), 7.52 (dd, J=8.6 Hz, 8.2, 3H), 7.33 (t, J=7.6 Hz, 1H), 7.21 (t, J=7.6 Hz, 1H), 7.07-7.02 (m, 2H), 6.72 (d, J=7.6 Hz, 1H), 4.19 (s, 2H); 13C NMR (100 MHz, d6-DMSO) δ141.78, 138.11, 133.87, 129.50, 128.31, 128.25, 127.90, 125.81, 124.42, 123.19, 121.01, 120.18, 119.75, 112.25, 109.59. 109.32.

Compound 12: 1-(3,5-diphenyl-4H-1,2,4-triazol-4-yl)-9-phenyl-9H-carbazole

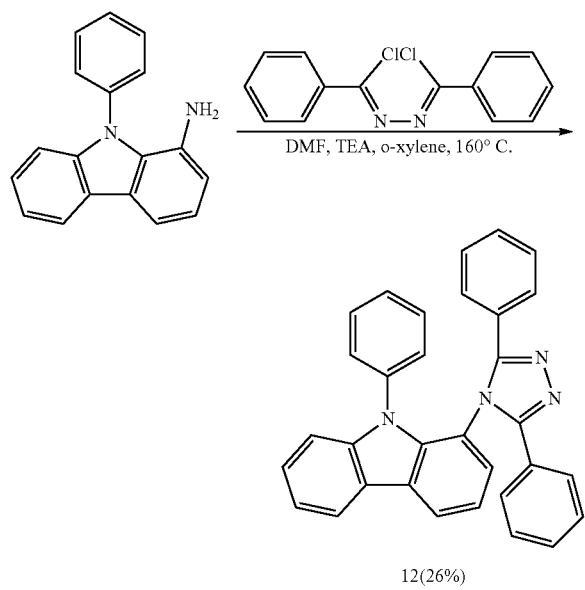

12(26%)

Compound 11 (0.27 g, 1.1 mmol), N-(chloro(phenyl)methylene) benzohydrazonoyl chloride (0.29 g, 1.1 mmol), triethylamine (0.29 mL, 2.1 mmol), N,N-dimethylforamide (0.16 mL, 2.1 mmol), and p-xylene (10.5 mL) are placed into a single neck flask (25 mL) and stirred with a magnetic stir bar. The erected condenser is heated to 160° C. and refluxed for 67 hours. Subsequently, the solvent is removed by vacuum distillation. After the mixture is heated and stirred with acetone for several hours, the solid is collected by suction filtration. Then, dichloromethane and ethanol are further used for recrystallization to obtain Compound 12, namely Compound O-3 (0.124 g, a yellowish solid), and the yield is 26%. After it sublimates, a white solid is obtained.

Spectral data as follow: mp. 244° C. 1H NMR (400 MHz, CD2Cl2) δ8.41 (dd, J=7.2 Hz, 1.2, 1H), 8.21-8.19 (m, 1H), 7.45-7.36 (m, 8H), 7.34-7.28 (m, 3H), 7.25-7.19 (m, 6H), 6.89 (dd, J=6.8 Hz, 1.2 Hz, 1H) 6.74-6.71 (m, 2H): 13C NMR (100 MHz, CD2Cl2) δ154.11, 143.18, 136.04, 135.71, 129.76, 129.62, 128.94, 128.65, 128.18, 128.11, 127.64, 127.41, 127.00, 122.85, 122.60, 121.16, 120.60, 120.58, 119.45, 110.75. HRMS (EI) m/z calcd for $C_{32}H_{22}N_4$ 462.1839, obsd. 462.1837. Anal. Calcd for $C_{32}H_{22}N_4$: C, 83.09; H, 4.79; N, 12.11. Found: C, 82.58; H, 4.85; N, 11.99.

Example 4: Synthesis of Compound O-4

Compound 13: 3,6-dinitro-9-phenyl-9H-carbazole

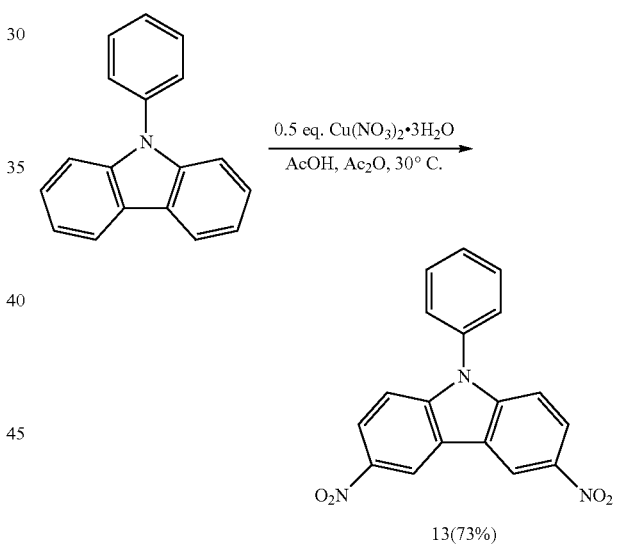

13(73%)

Copper nitrate trihydrate (1.04 g, 4.30 mmol), acetic acid (15 mL), and acetic anhydride (2.5 mL) are placed into a single neck flask (50 mL) and stirred with a magnetic stir bar for 10 minutes. 9-phenylcarbazole (0.40 g, 1.6 mmol) is added and then stirred in water bath at 30° C. for 30 minutes. Subsequently, deionized water (20 mL) is added to yield a yellow solid. The solid is collected by suction filtration and washed with deionized water several times. Then, o-dichlorobenzene is used for recrystallization to obtain Compound 13 (0.40 g, a yellow solid), and the yield is 73%.

Spectral data as follow: $^1$H NMR (400 MHz, CDCl$_3$) δ9.13 (d, J=1.6 Hz, 2H), 8.40 (dd, J=9.2 Hz, 2.4 Hz, 2H), 7.70 (t, J=7.6 Hz, 2H), 7.62 (t, J=7.6 Hz, 1H), 7.53 (d, J=7.6 Hz, 2H), 7.42 (d, J=8.8 Hz, 2H); $^{13}$C NMR (100 MHz, CDCl$_3$) δ145.54, 142.78, 135.44, 130.90, 129.89, 127.32, 123.44, 123.01, 117.98, 110.96.

Compound 14: 9-phenyl-9H-carbazole-3,6-diamine

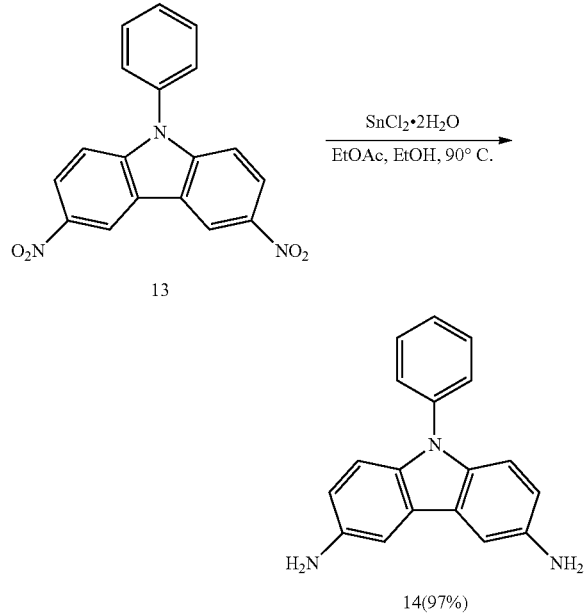

Compound 13 (1.2 g, 3.6 mmol), tin(II) chloride dihydrate (8.12 g, 36.0 mmol), ethyl acetate (18 mL), and ethanol (18 mL) are placed into a single neck flask (50 mL) and stirred with a magnetic stir bar. Subsequently, the erected condenser is heated to 90° C. and refluxed for 10 hours. After the mixture cools to room temperature, it is poured into 2 M aqueous solution of potassium hydroxide and then extracted with ethyl acetate to collect the organic layer. The organic layer is dried over anhydrous magnesium sulfate and then the solvent is removed by a rotary concentration to obtain Compound 13 (0.95 g, a gray solid), and the yield is 97%.

Spectral data as follow: $^1$H NMR (400 MHz, $d_6$-DMSO) δ7.58 (t, J=7.6 Hz, 2H), 7.50 (d J=7.6 Hz, 2H), 7.36 (t, J=7.6 Hz, 1H), 7.13-710 (m, 4H), 6.69 (dd, J=8.6 Hz, 2.1 Hz, 2H), 4.78 (s, 4H); $^{13}$C NMR (100 MHz, CDCl$_3$) 139.41, 138.56, 135.75, 129.71, 126.53, 126.49, 123.89, 115.79, 110.47, 105.98.

Compound 15: 3,6-bis(3,5-diphenyl-4H-1,2,4-triazol-4-yl)-9-phenyl-9H-carbazole

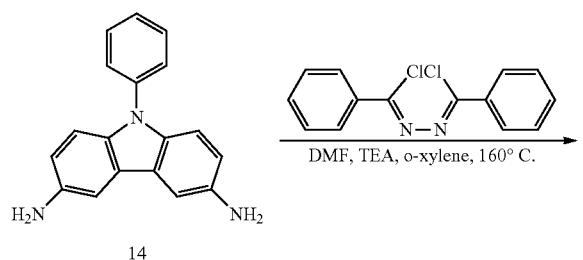

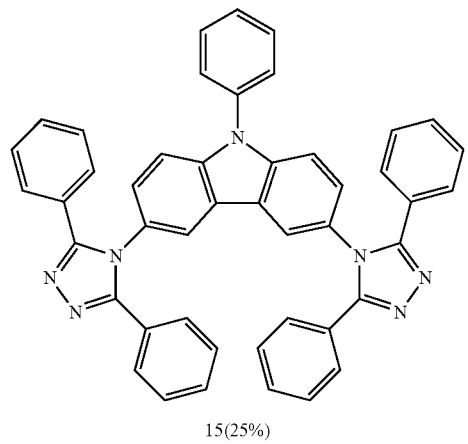

Compound 14 (0.95 g, 3.5 mmol), N-(chloro(phenyl)methylene) benzohydrazonoyl chloride (1.93 g, 6.96 mmol), triethylamine (1.94 mL, 13.9 mmol), NA-dimethylforamide (1.08 mL, 14.0 mmol), and p-xylene (17.4 mL) are placed into a single neck flask (50 mL) and stirred with a magnetic stir bar. The erected condenser is heated to 160° C. and refluxed for 85 hours. Subsequently the solvent is removed by vacuum distillation. After the mixture is heated and stirred with acetone for several hours, a solid is collected by suction filtration. Dichloromethane and ethanol are further used for recrystallization to obtain Compound 15, i.e. Compound O-4 (0.59 g, a yellowish brown solid), and the yield is 25%. After it sublimates, a white solid is obtained.

Spectral data as follow: mp. 385° C. $^1$H NMR (400 CD$_2$Cl$_2$) δ7.79 (d, J=2.0 Hz, 2H), 7.69-7.65 (m, 2H), 7.62-7.60 (m, 2H), 7.56 (tt, J=7.2 Hz, 1.4 Hz, 1H), 7.47-7.43 (m, 10H), 7.36-7.30 (m, 5H), 7.28-7.24 (m, 9H); $^{13}$C NMR (100 MHz, CD$_2$Cl$_2$) δ155.66, 141.98, 136.66, 130.82, 130.05, 129.31, 129.17, 128.92, 128.52, 127.86, 127.42, 127.16, 123.58, 120.78, 111.90. HRMS (EI) calcd for C$_{46}$H$_{31}$N$_7$ 681.2635, obsd. 681.2646. Anal. Calcd for C$_{46}$H$_{31}$N$_7$: C, 81.04; H, 4.58; N, 14.38. Found: C, 81.20; H, 4.39; N, 14.72.

Example 5: Synthesis of Compound O-5

Compound 16: 9-(2,6-dinitrophenyl)-9H-carbazole

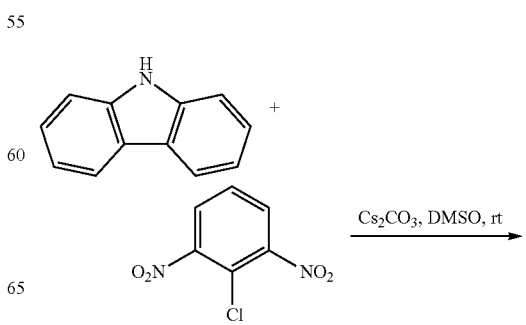

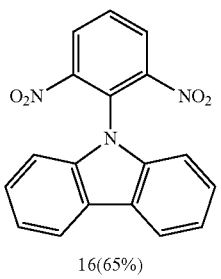

16(65%)

Carbazole (0.65 g, 3.9 mmol), 2-chloro-1,3-dinitrobenzene (0.79 g, 3.9 mmol), and dimethylsulfoxide (10.8 mL) are placed into a single neck flask (25 mL) After stirred with a magnetic stir bar until solids dissolve followed by adding cesium carbonate (1.52 g, 4.68 mmol), then they react at room temperature for 18 hours. Deionized water (10 mL) is added to generate a yellow solid. It is then extracted with trichloromethane several times. The organic layer is collected and then washed with deionized water several times. The organic layer is dried over anhydrous magnesium sulfate and then the solvent is removed by a rotary concentration. The column chromatography is performed with the eluent (ethyl acetate:n-hexane=1:3) to obtain an orange-brown solid. Then, after it is heated and stirred with methanol for half an hour, Compound 17 (0.84 g, a yellow solid) is obtained by the suction filtration, and the yield is 65%.

Spectral data as follow: $^1$H NMR (400 MHz, CDCl$_3$) δ8.29 (d, J=8.0 Hz, 2H), 8.09 (d, J=7.6 Hz, 2H), 7.89 (t, J=8.0 Hz, 1H), 7.37 (t, J=8.0 Hz, 2H), 7.31 (t, J=7.2 Hz, 2H), 6.99 (d, J=8.0 Hz, 2H); $^{13}$C NMR (100 MHz, d$_6$-DMSO) δ148.53, 140.00, 132.01, 129.93, 126.59, 123.20, 123.13, 120.97, 120.65, 109.00. HRMS (EI) m/z calcd for C$_{18}$H$_{11}$O$_4$N3 333.0744, obsd. 333.0741.

Compound 17:
2-(9H-carbazol-9-yl)benzene-1,3-diamine

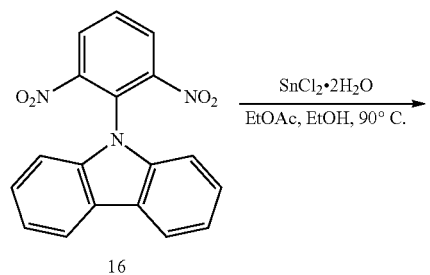

Compound 16 (0.70 g, 2.1 mmol), tin(II) chloride dihydrate (4.74 g, 21.0 mmol), ethyl acetate (10.5 mmol), and ethanol (10.5 mmol) are placed into a single neck flask (50 mL) and stirred with a magnetic stir bar. After the erected condenser is heated to 90° C. and refluxed for 10 hours, it becomes a yellowish clear solution. After the solution cools to room temperature, it is poured into 2 M aqueous solution of potassium hydroxide and then extracted with ethyl acetate to collect the organic layer. The organic layer is dried over anhydrous magnesium sulfate and then the solvent is removed by a rotary concentration to obtain Compound 17 (0.57 g, a white solid), and the yield is 100%.

Spectral data as follow: $^1$H NMR (400 MHz, CDCl$_3$) δ8.15 (d, J=8.0 Hz, 2H), 7.41 (td, J=7.3 Hz, 1.1 Hz, 2H), 7.31-7.27 (m, 2H), 7.19 (d, J=8.4 Hz, 2H), 7.09 (t, J=8.0 Hz, 1H), 6.30 (d, J=8.4 Hz, 2H), 3.34 (s, 4H); $^{13}$C NMR (100 MHz, CDCl$_3$) δ145.68, 139.76, 130.44, 126.45, 123.68, 120.65, 120.40, 110.24, 108.22, 105.82. HRMS m/z calcd for C$_{18}$H$_{16}$N$_3$ 274.1344 (M++H), obsd. 274.1355 (M++H).

Compound 18: 9-(2,6-bis(3,5-diphenyl-4H-1,2,4-triazol-4-yl)phenyl)-9H-carbazole

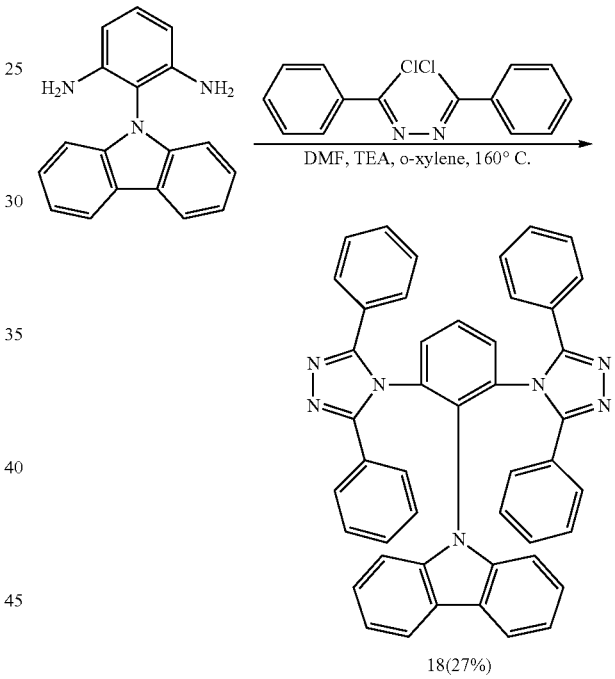

18(27%)

Compound 17 (0.67 g, 2.5 mmol), N'-(chloro(phenyl)methylene) benzohydrazonoyl chloride (1.56 g, 5.63 mmol), triethylamine (3.14 mL, 22.5 mmol), N,N-dimethylforamide (1.74 mL, 22.5 mmol), and p-xylene (25.6 mL) are placed into a single neck flask (100 mL) and stirred with a magnetic stir bar. The erected condenser is heated to 160° C. and refluxed for 72 hours. Subsequently the solvent is removed by vacuum distillation. After the mixture is heated and stirred with acetone for several hours, a solid is collected by suction filtration. The column chromatography is performed with the eluent (ethyl acetate:dichloromethane=1:1) to obtain a white solid. Then, dichloromethane and ethanol are further used for recrystallization to obtain Compound 18, i.e. Compound O-5 (0.445 g, a white crystal), and the yield is 27%.

Spectral data as follow: mp. >442° C. $^1$H NMR (400 MHz, CD$_2$Cl$_2$) δ8.15 (d, J=8.0 Hz, 2H), 8.01 (dd, J=8.0 Hz, 7.2 Hz, 1H) 7.74 (d, J=8.0 Hz, 2H), 7.32-7.27 (m, 4H), 7.18-7.13 (m, 16H), 6.92-6.88 (m, 2H), 6.26-6.21 (m, 2H), 5.32 (d, J=8.0 Hz, 2H); $^{13}$C NMR (100 MHz, CD$_2$Cl$_2$) δ154.17, 138.79, 136.43, 134.40, 133.51, 130.60, 129.95, 128.97, 128.51, 126.97, 126.25, 123.61, 120.61, 119.73, 109.42. HRMS (ESI) m/z calcd for C$_{46}$H$_{32}$N$_7$ 682.2714 (M++H), obsd. 682.2713 (M++H). Anal. Calcd for C$_{46}$H$_{31}$N$_7$: C, 81.04; H, 4.58; N, 14.38. Found: C, 81.63; H, 4.51; N, 14.40.

Example 6: Evaluation Methods for the Organic Electroluminescent Material

The evaluation methods of the embodiment is related to the host material of the organic electroluminescent material, namely the measurements of the triplet energy gap ($E_T$), the glass transition temperature ($T_g$), the pyrolysis temperature (Td), the highest occupied molecular orbital energy gap (HOMO), and the lowest unoccupied molecular orbital energy gap (LUMO) which are performed on above mentioned Compound O-1, Compound O-2, Compound O-3, Compound O-4, and Compound O-5, respectively. Furthermore, in the embodiment, the conventional host material N,N'-dicarbazolyl-3,5-benzene (mCP) acts as a control group, the guest material of the embodiment is FIrpic (i.e. compound of Formula (5)) for example, and the triplet energy gap ($E_T$) of FIrpic is generally 2.7 eV Here, the glass transition temperature ($T_g$) is measured by a differential scanning calorimeter (DSC). Temperature at which the material loses 5 vol % volume is measured by a thermogravimetric analyzer (TGA), and the temperature acts as the pyrolysis temperature. The results are shown in Table 1.

TABLE 1

The evaluation results of Compound O-1 to O-5 of the organic electroluminescent material.

| | $E_T$ (eV) | $T_g$ (° C.) | $T_d$ (° C.) | HOMO (eV) | LUMO (eV) |
|---|---|---|---|---|---|
| Compound O-1 | 3.09 | — | 358 | 5.84 | 2.25 |
| Compound O-2 | 3.11 | — | 380 | 5.74 | 2.15 |
| Compound O-3 | 3.06 | — | 345 | 5.90 | 2.10 |
| Compound O-4 | 3.11 | 173 | 447 | 5.98 | 2.44 |
| Compound O-5 | 3.09 | — | 458 | 5.90 | 2.42 |
| Control group | 2.90 | 55 | — | 5.9 | 2.4 |

From Table 1, although the triplet energy gap (2.90 eV) of the control group is higher than the triplet energy gap (2.7 eV) of FIrpic of the guest material, the glass transition temperature ($T_g$) of the control group is only 55° C., and thereby the thermal stability of the control group is poor. The triplet energy gaps of Compound O-1, O-2, O-3, O-4, and O-5 are higher than 3.0 eV, and thus they are also higher than the triplet energy gaps of the control group and FIrpic. Therefore, Compound O-1, O-2, O-3, O-4, and O-5 of the embodiment may be indeed suitable to the organic electroluminescent device which has the blue guest material, and its luminous efficiency is better than that of the control group (that will be further explained by example 7 later).

In addition, the glass transition temperature ($T_g$) of Compound O-4 is 173° C. and thus it has the fine thermal stability. However, the glass transition temperature ($T_g$) of Compound O-1, O-2, O-3, and O-5 cannot be observed. Because two aromatic groups of Compound O-1, O-2, O-3, and O-5 are ortho-substitution in the benzene ring, the molecules present non-coplanar structures and it is not easy for them to stack between the compound molecules. Therefore, they have relatively fine thermal stability.

Moreover, Table 1 shows that the pyrolysis temperatures of Compound O-1, O-2, O-3, O-4 and O-5 are higher than 340° C. The reason is that their structures contain multiple benzene rings which belong to rigid structures, so that the pyrolysis caused by the heat is not easily occurred during the heating process. For the above reasons, the carbazole derivatives of Compound O-1, O-2, O-3, O-4 and O-5 which have excellent thermal stability and high triplet energy gap may act as the excellent organic electroluminescent material, and they are conducive to the application of acting as the host material in the organic luminescent layer 233.

The following is another example which illustrates the application of Compound O-1 to O-5 (carbazole derivatives) to the organic electroluminescent device and verifies the luminous efficiency of the organic electroluminescent device.

Example 7: The Luminous Efficiency of the Organic Electroluminescent Device

The example illustrates the manufacturing method for the organic electroluminescent device according to the embodiment and detects its luminous efficiency.

Referring to FIG. 2, the manufacturing method for the organic electroluminescent devices 2 (2-1 to 2-16) of the embodiment is the evaporation, the material of the first electrode layer 21 is ITO, and that of the second electrode layer 22 is aluminum. One side of the first electrode layer 21 is plated with a hole transport material NPB to form the hole transport layer. Then, it is plated with mCP as the exciton blocking layer 232 to assist in the injection of the electron hole and prevent the exciton from entering the hole transport layer 231 from the organic luminescent layer 233. Moreover, the material of the electron transport layer 234 is TAZ, and that of the electron injection layer 235 may be DPPS or TAZ.

Here, as to the organic luminescent layer 233, Compound O-1 (carbazole derivative) acts as the host material and meantime FIrpic (i.e. compound of Formula (5)) of different doping proportions acts as the guest material, and thus the organic electroluminescent devices 2-1 to 2-5 are formed dependent on FIrpic of different doping proportions. Furthermore, the organic electroluminescent devices 2-6 to 2-10 are formed by Compound O-2 acting as the host material and meantime FIrpic of different doping proportions acting as the guest material. The organic electroluminescent devices 2-11 to 2-12 are formed by Compound O-3 acting as the host material and meantime FIrpic of different doping proportions acting as the guest material. The organic electroluminescent devices 2-13 to 2-14 are formed by Compound O-4 acting as the host material and meantime FIrpic of different doping proportions acting as the guest material. The organic electroluminescent devices 2-15 to 2-16 are formed by Compound O-5 acting as the host material and meantime FIrpic of different doping proportions acting as the guest material.

Electric currents are injected into the organic electroluminescent devices 2-1 to 2-16 manufactured in example 7, and the driving voltage (V), the maximum current efficiency (cd/A), the maximum power efficiency (lm/W), and the maximum external quantum efficiency (EQE), whose unit is %, of the organic electroluminescent devices 2-1 to 2-16 are detected at the current density of 50 mA/cm$^2$. The evaluation results are shown in Table 2.

TABLE 2

The luminous efficiency of the organic electroluminescent devices 2-1 to 2-16.

| organic electroluminescent | | proportion of FIrpic (vol %) | driving voltage (V) | current efficiency (cd/A) | power efficiency (lm/W) | EQE (%) |
|---|---|---|---|---|---|---|
| O-1 host material | 2-1 | 0 | 8.53 | 1.12 | 0.88 | 1.42 |
| | 2-2 | 9 | 9.13 | 28.86 | 21.87 | 11.75 |
| | 2-3 | 12 | 8.87 | 31.05 | 21.70 | 12.55 |
| | 2-4 | 15 | 8.99 | 33.88 | 25.14 | 13.60 |
| | 2-5 | 18 | 9.10 | 30.69 | 22.44 | 11.42 |
| O-2 host material | 2-6 | 0 | 7.02 | 0.6 | 0.31 | 0.7 |
| | 2-7 | 9 | 9.90 | 30.58 | 24.02 | 9.23 |
| | 2-8 | 12 | 9.54 | 32.06 | 24.77 | 9.46 |
| | 2-9 | 15 | 9.23 | 32.90 | 25.4 | 9.9 |
| | 2-10 | 18 | 8.71 | 33.7 | 26.3 | 10.71 |
| O-3 host material | 2-11 | 9 | 9.15 | 45.26 | 35.06 | 14.74 |
| | 2-12 | 15 | 9.13 | 46.48 | 36.51 | 17.62 |
| O-4 host material | 2-13 | 9 | 11.32 | 40.42 | 31.74 | 8.3 |
| | 2-14 | 15 | 11.56 | 44.95 | 34.55 | 13.37 |
| O-5 host material | 2-15 | 9 | 11.26 | 40.2 | 31.6 | 14.74 |
| | 2-16 | 15 | — | 45.6 | 35.9 | 17.62 |

Above mentioned example 6 shows that when Compound O-1 to O-5 (carbazole derivatives) act as the host material, compared with conventional mCP, they have excellent thermal stability and high triplet energy gap. Further, Table 2 (results) of example 7 shows that Compound O-1 to O-5 (carbazole derivatives) are indeed suitable to act as the organic electroluminescent devices to emit light. Moreover, the results of the luminous efficiency of the organic electroluminescent devices 2-1 to 2-16 with the guest material of different doping proportion are provided in example 7. Therefore, the organic electroluminescent device may be adjusted to have preferable current efficiency, preferable power efficiency, and preferable external quantum efficiency by the guest material of different doping proportion. In the embodiment, the doping proportion of the guest material may be between 5 vol % and 40 vol %. Preferably, when the host material is Compound O-1 or Compound O-2, the doping proportion of the guest material FIrpic may be 9 vol % to 18 vol %, more preferably be 15 vol %; when the host material is Compound O-3, Compound O-4, or Compound O-5, the doping proportion of the guest material FIrpic may be 9 vol % to 15 vol %.

Moreover, the quantum dot electroluminescent unit according to the disclosure, like the above mentioned organic luminescent unit 23, is disposed between the first electrode layer 21 and the second electrode layer 22. The quantum dot electroluminescent unit includes a plurality of electro-phosphorescent quantum dots and at least an organic electroluminescent material. The electro-phosphorescent quantum dots disperse in the organic electroluminescent material. The details of the components and material of the quantum dot electroluminescent unit may refer to the technical contents of the organic luminescent unit according to the above mentioned embodiments so they are not repeated here.

Figure 3:
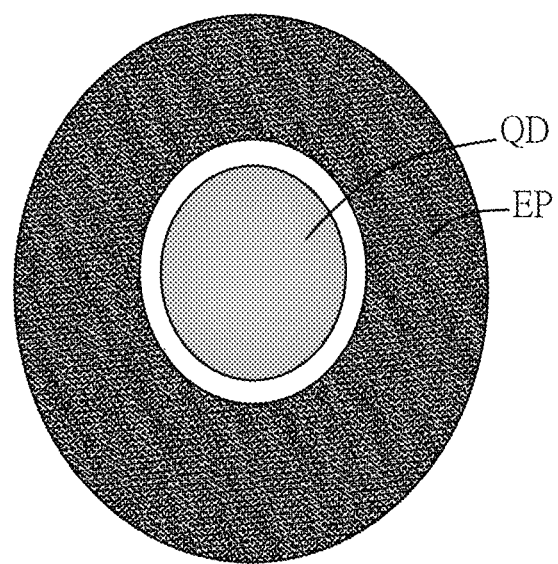
FIG. 3 is a schematic diagram of an electro-phosphorescent quantum dot according to the invention.

FIG. 3 is a schematic diagram of an electro-phosphorescent quantum dot according to the disclosure. Referring to FIG. 3, the electro-phosphorescent quantum dot of the embodiment refers to a quantum dot QD coated with a phosphorescent material EP. The quantum dot QD may be an inorganic semiconductor particle. Specifically, the phosphorescent material EP is attached to the quantum dot QD in a manner of spin coating or vapor deposition. The term "attached" of the embodiment includes being attached by a covalent bond, an ionic bond, a hydrogen bond, van der Waals force, or other chemical bonds. Moreover, the phosphorescent material EP may further include a linker, for example having thiophene, amino, hydroxyl, thiol, alkenyl, alkynyl, ether, thioether, phosphine, amide, carboxyl, sulfonate, phosphate, silane, or sulfide groups, so that the phosphorescent material EP may be attached to the quantum dot QD by the linker to form the electro-phosphorescent quantum dot of the embodiment.

Moreover, the organic electroluminescent material is a host material, and the electro-phosphorescent quantum dots are a guest material. The content of the guest material in the organic electroluminescent material is between 1 vol % and 50 vol %.

In summary, as to the organic electroluminescent material, the organic electroluminescent device and the quantum dot electroluminescent unit of the present invention, the organic electroluminescent material includes the above Formula (1) and Formula (2) and has the excellent thermal stability and the high triplet energy gap. Compared with the conventional technique, the present invention may improve the luminous efficiency and the thermal stability of the organic electroluminescent device.

Although the invention has been described with reference to specific embodiments, this description is not meant to be construed in a limiting sense. Various modifications of the disclosed embodiments, as well as alternative embodiments, will be apparent to persons skilled in the art. It is, therefore, contemplated that the appended claims will cover all modifications that fall within the true scope of the invention.

What is claimed is:

1. An organic electroluminescent material, comprising a structure of the following Formula (1),

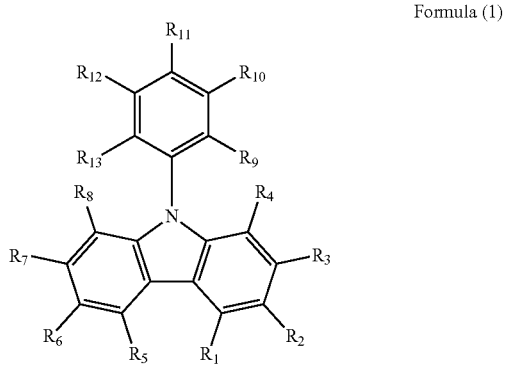

Formula (1)

wherein one of $R_2$, $R_4$ or $R_6$, or two of $R_2$, $R_4$, $R_6$, $R_9$, or $R_{13}$ are independent triazole derivatives, and the triazole derivatives have the structure of the following Formula (2),

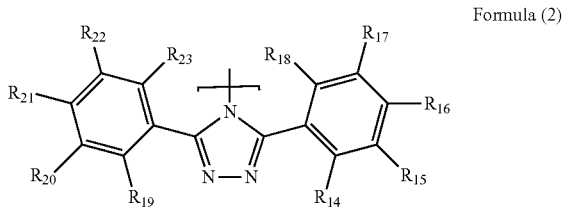

Formula (2)

the other substituents of $R_1$ to $R_{23}$ are independently selected from the group consisting of a hydrogen atom, a fluorine atom, a cyano group, an alkyl group, a cycloalkyl group, an alkoxy group, a thioalkyl group, a silyl group, and an alkenyl group.

2. The organic electroluminescent material of claim 1, wherein $R_1$, $R_3$, $R_5$, $R_7$, $R_8$, $R_{10}$ to $R_{12}$, and $R_{14}$ to $R_{23}$ are independently selected from the group consisting of a substituted straight-chain alkyl group with the carbon number of 1 to 6, a non-substituted straight-chain alkyl group with the carbon number of 1 to 6, a substituted branched-chain alkyl group with the carbon number of 1 to 6, a non-substituted branched-chain alkyl group with the carbon number of 1 to 6, a substituted cycloalkyl group with the carbon number of 1 to 6, a non-substituted cycloalkyl group with the carbon number of 1 to 6, a substituted straight-chain alkoxy group with the carbon number of 1 to 6, a non-substituted straight-chain alkoxy group with the carbon number of 1 to 6, a substituted branched-chain alkoxy group with the carbon number of 1 to 6, a non-substituted branched-chain alkoxy group with the carbon number of 1 to 6, a substituted straight-chain thioalkyl group with the carbon number of 1 to 6, a non-substituted straight-chain thioalkyl group with the carbon number of 1 to 6, a substituted branched-chain thioalkyl group with the carbon number of 1 to 6, a non-substituted branched-chain thioalkyl group with the carbon number of 1 to 6, a substituted straight-chain silyl group with the carbon number of 1 to 6, a non-substituted straight-chain silyl group with the carbon number of 1 to 6, a substituted branched-chain silyl group with the carbon number of 1 to 6, a non-substituted branched-chain silyl group with the carbon number of 1 to 6, a substituted straight-chain alkenyl group with the carbon number of 1 to 6, a non-substituted straight-chain alkenyl group with the carbon number of 1 to 6, a substituted branched-chain alkenyl group with the carbon number of 1 to 6, and a non-substituted branched-chain alkenyl group with the carbon number of 1 to 6.

3. The organic electroluminescent material of claim 1, wherein when $R_2$ is the triazole derivative, $R_1$ and $R_3$ to $R_{23}$ are hydrogen atoms.

4. The organic electroluminescent material of claim 1, wherein when $R_4$ is the triazole derivative, $R_1$ to $R_3$ and $R_5$ to $R_{23}$ are hydrogen atoms.

5. The organic electroluminescent material of claim 1, wherein when $R_2$ and $R_6$ are the triazole derivatives, $R_1$, $R_3$ to $R_5$ and $R_7$ to $R_{23}$ are hydrogen atoms.

6. The organic electroluminescent material of claim 1, wherein when $R_9$ and $R_{13}$ are the triazole derivatives, $R_1$ to $R_8$, $R_{10}$ to $R_{12}$ and $R_{14}$ to $R_{23}$ are hydrogen atoms.

7. An organic electroluminescent device, comprising:
a first electrode layer;
a second electrode layer; and
an organic luminescent unit, disposed between the first electrode layer and the second electrode layer, wherein the organic luminescent unit has at least an organic electroluminescent material, and the organic electroluminescent material has a structure of the following Formula (1),

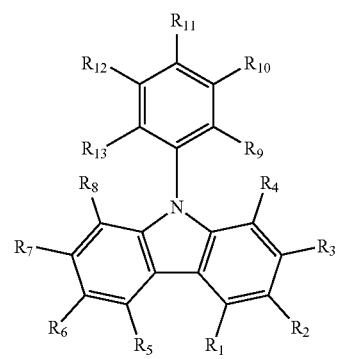

Formula (1)

wherein one of $R_2$, $R_4$ or $R_6$, or two of $R_2$, $R_4$, $R_6$, $R_9$, or $R_{13}$ are independent triazole derivatives, and the triazole derivatives have the structure of the following Formula (2),

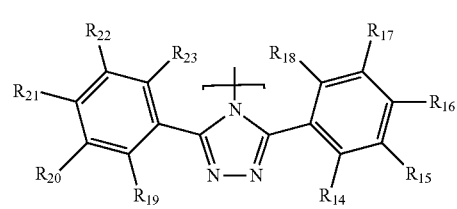

Formula (2)

the other substituents of $R_1$ to $R_{23}$ are independently selected from the group consisting of a hydrogen atom, a fluorine atom, a cyano group, an alkyl group, a cycloalkyl group, an alkoxy group, a thioalkyl group, a silyl group, and an alkenyl group.

8. The organic electroluminescent device of claim 7, wherein the organic electroluminescent material is selected from the group consisting of compounds of following O-2 to O-5:

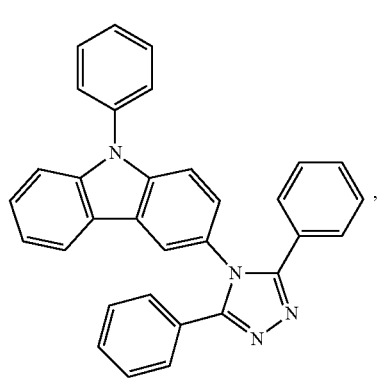

O-2

-continued

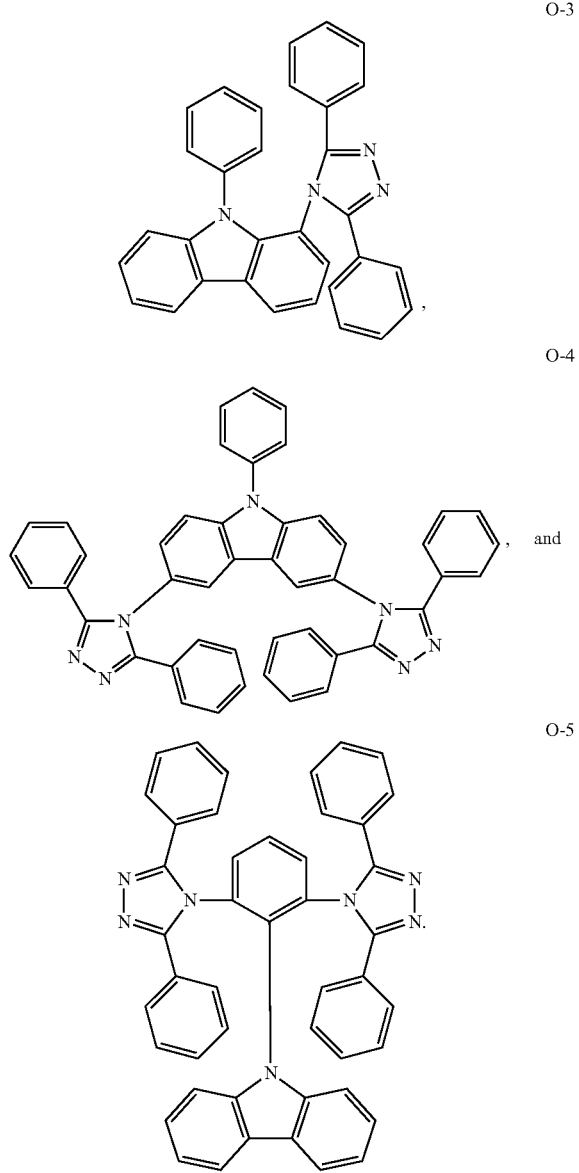

O-3,

O-4, and

O-5.

9. The organic electroluminescent device of claim 7, wherein the organic luminescent unit comprises an organic luminescent layer, a hole transport layer and an electron transport layer, and the organic luminescent layer is disposed between the hole transport layer and the electron transport layer.

10. The organic electroluminescent device of claim 9, wherein the organic luminescent unit further comprises an exciton blocking layer and an electron injection layer, and the exciton blocking layer, the organic luminescent layer, and the electron transport layer are in turn disposed between the hole transport layer and the electron injection layer.

11. The organic electroluminescent device of claim 9, wherein the organic luminescent layer comprises a host material and a guest material, the host material is the organic electroluminescent material, and the guest material is a phosphorescent material.

12. The organic electroluminescent device of claim 11, wherein the guest material comprises one of the compounds of the following Formula (3) to (5):

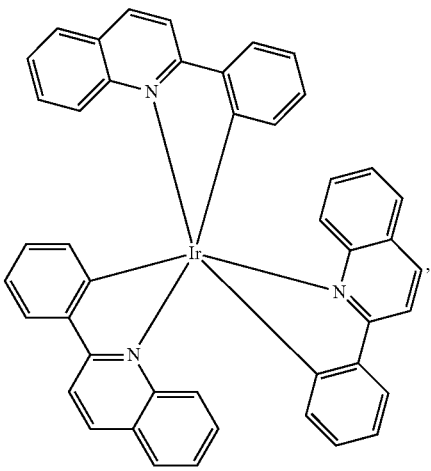

Formula (3)

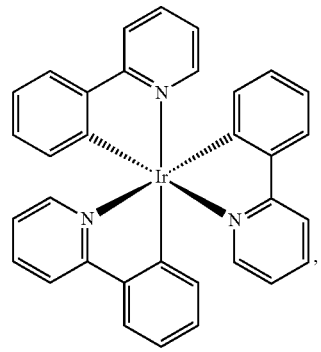

Formula (4)

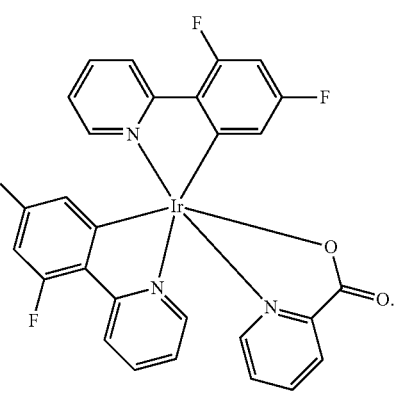

Formula (5)

13. The organic electroluminescent device of claim 11, wherein the content of the host material in the organic luminescent layer is between 60 vol % to 95 vol %.

14. The organic electroluminescent device of claim 11, wherein the content of the guest material in the organic luminescent layer is between 5 vol % to 40 vol %.

15. A quantum dot electroluminescent unit, comprising a plurality of electro-phosphorescent quantum dots and at least an organic electroluminescent material, wherein the electro-phosphorescent quantum dots disperse in the organic electroluminescent material, and the organic electroluminescent material comprises a structure of the following Formula (1),

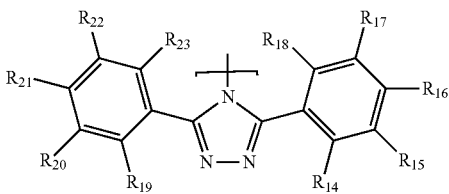

Formula (2)

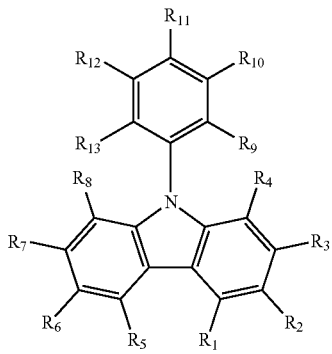

Formula (1)

wherein one or two of $R_2$, $R_4$, $R_6$, $R_9$ or $R_{13}$ are independent triazole derivatives, and the triazole derivatives have the structures of the following Formula (2), the other substituents of $R_1$ to $R_{23}$ are independently selected from the group consisting of a hydrogen atom, a fluorine atom, a cyano group, an alkyl group, a cycloalkyl group, an alkoxy group, a thioalkyl group, a silyl group, and an alkenyl group.

16. The quantum dot electroluminescent unit of claim 15, wherein the electro-phosphorescent quantum dots are inorganic semiconductor particles coated with a phosphorescent material.

17. The quantum dot electroluminescent unit of claim 15, wherein the electro-phosphorescent quantum dots comprise a transition metal.

18. The quantum dot electroluminescent unit of claim 15, wherein the organic electroluminescent material is a host material, and the electro-phosphorescent quantum dots are a guest material.

19. The quantum dot electroluminescent unit of claim 18, wherein the content of the guest material in the organic electroluminescent material is between 1 vol % and 50 vol %.

* * * * *